(12) United States Patent
Morrow et al.

(10) Patent No.: US 6,225,086 B1
(45) Date of Patent: May 1, 2001

(54) POLYNUCLEOTIDES ENCODING ANKYRIN PROTEINS

(75) Inventors: Jon S. Morrow, Madison; Prasad Devarajan, North Haven, both of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/082,059

(22) Filed: May 21, 1998

Related U.S. Application Data

(60) Provisional application No. 60/047,356, filed on May 21, 1997.

(51) Int. Cl.$^7$ .................................................. C12N 15/00
(52) U.S. Cl. ............... 435/69.1; 435/320.1; 435/252.3; 530/350; 536/23.1; 536/23.5
(58) Field of Search ..................... 435/320.1, 2, 69.1, 435/252.3; 536/23.1, 23.5; 530/350

(56) References Cited

U.S. PATENT DOCUMENTS 5,824,306 * 10/1998 Tang et al. .................. 424/130.1
5,989,863 * 11/1999 Tang et al. .................. 435/69.1

OTHER PUBLICATIONS

Hoock et al. The Journal of Cell Biology, vol. 136, pp. 1059–1070, Mar. 10, 1997.*
Kordeli E, et al. AnkyrinG. A new ankyrin gene with neural–specific isoforms localized at the axonal initial segment and node of Ranvier. J Biol Chem., Feb. 1995, vol. 270, p. 2352–9.*
Devarajan, P. et al., "Na,K–ATPase Transport From Endoplasmic Reticulum to Golgi Requires the Golgi Spectrin–Ankyrin G119 Skeleton in Madin Darby Canine Kidney Cells", *Proc. Natl. Acad. Sci.*, (Sep. 1997), vol. 94, pp. 10711–10716.

Kennedy, S.P. et al., "Ankyrin Binds to the 15th Repetitive Unit of Erythroid and Nonerythroid β–Spectrin", *Journal of Cell Biology*, (Oct. 1991), vol. 115, pp. 267–277.
Devarajan, P. et al., "Ankyrin Binds to Two Distinct Cytoplasmic Domains of Na,K–ATPase α Subunit", *Proc. Natl. Acad. Sci.*, (Apr. 1994), vol. 91, pp. 2965–2969.
Devarajan, P. et al., "Identification of a Small Cytoplasmic Ankyrin (Ank$_{G119}$) in the Kidney and Muscle the Binds βIΣ* Spectrin and Associates with the Golgi Apparatus", *Journal of Cell Biology*, (May 1996) vol. 133, pp. 819–830.
Lombardo, C.R. et al., "βII–Spectrin (Fodrin) and βIΣ2–Spectrin (Muscle) Contain NH$_2$–and COOH–terminal Membrane Association Domains (MAD1 and MAD2)", *Journal of Biological Chemistry*, (Nov. 1994), vol. 269, pp. 29212–29219.
Beck et al., "The Spectrin–Based Membrane Skeleton as a Membrane Protein–Sorting Machine", *Amer. J. Physiology*, (May 1996), vol. 270, pp. C1263–70.
Beck et al. "Golgi Spectrin: Identification of an Erythroid β–Spectrin Homolog Associated With the Golgi Complex", *Journal of Cell Biology*, (Nov. 1994), vol. 127, pp. 707–723.

* cited by examiner

*Primary Examiner*—Ponnathapu Achutamurthy
*Assistant Examiner*—Bradley S. Mayhew
(74) *Attorney, Agent, or Firm*—Morgan, Lewis & Bockius LLP

(57) ABSTRACT

A novel cytoplasmic ankyrin protein is disclosed along with methods for selectively identifying ankyrin proteins that participate in the trafficking of integral membrane proteins and secretory proteins between the endoplasmic reticulum, Golgi and other membrane compartments. Nucleic acid and protein sequences are disclosed, along with methods for identifying agents that modulate the binding of ankyrins to their binding partners.

11 Claims, 14 Drawing Sheets

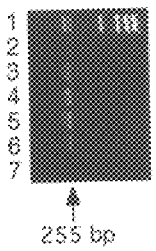

Ank_B family
2  TTPLTFVNECVSFTTNVSARFWLIDCRQIQESVTFASQVYREIICVPYMAKFVVFAKSHDPIEARLRCF
3  TTPLTFVNECVSFTTNVSARFWLIDCRQIQESVTFASQVYFEIICVPYMAKFVVFAKSHDPIEARLRCF
4  TTPLTFVNECVSFTTNVSARFWLIDCRQIQESVTFASQVYFEIICVPYMAKFVVFAKSHDPIEARLRCF
5  TTPLLYVNECVSFTTNVSARFWLIDCRQIQESVTFASQVYFEIICVPYMAKFRHFAKSHDPIEARVRCY
6  TTPLTFVNECVSFTTNVSARFWLIDCRQIQESVTFASQVYREIICVPYMAKFVVFAKSHDPIEARYRCY
Con TTPL--VNECVSFTTNVSARFWLIDCRQIQESVTFASQVY-EIICVPYMAKF---FAKSHDPIEAR-RC- Ank_G family
2  TTPLTFIKDCVSFTTNVSARFWLADCHQVLETVGLAFGVYREFICVPYMAKFVVFAKTNHPVEFFLSDL
3  TTPLTFIKDCVSFTTNVSARFWLADCHQVLETVGFALNLYREFICVPYMAKFVVFAKTNDPVESSLRYF
4  TTPLTFIKDCVSFTTNVSARFWLADCHQVLETVGFALNLYREFICVPYMAKFVVFAKTNDPVESSLRYF
5  TTPLTFIKDCVSFTTNVSARFWLADCHQVLETVGLATNLYREFICVPYMAKFVVFAKTNHPVESSLRCY
6  TTPLTFIKDCVSFTTNVSARFWLADCHQVLETVGLATQLYREFICVPYMAKFVVFAKTNDPVESSLRCF
Con TTPLTFIKDCVSFTTNVSARFWLADCHQVLETVG-A---YREFICVPYMAKFVVFAKTN-PVE--L---

```
AnkR  TTKLVVANECANFTTNVSARFWLSDCPRTAEAVNFATLLYKELTAVPYMAKFVVFAKMNDPREGRLRCF
AnkB  --P-TFV---VS---------I--RQIQ-S-T--SQV-R-IIC----------SH---I-A------
AnkG  --P-TFIKD-VS---------A--HQVL-T-GL-FGV-R-FIC----------TNH-V-FF--DL
```

FIG. 2a

```
GGAGCTCTTCTCACTCAAGCCCGAGTTCTATGTTCAGACATAGTTCATCACTGTGTCCTTCCAGATTTGGAAGCTGACAAAACACCATTCCAGTAGCT    105
                                                                                   · R1
GCATCTCCAGGTTTTGAGTCTAGAAATGAATTAAGATGTGATCTCTTGGATAAGAAATGCCAAATGCCCTTACCCCTCTTCATAT                210
 M  N  L  R  C  D  L  L  D  K  K  A  N  P  N  A  K  A  L  N  G  F  T  P  L  H  I                    27
                                                    · R2
TGCCTGCAAGAAGAATCGAATTAAGAAATGGAACTCCTTCTGAAACACGGTGCATCTCAAGCTGTAACCGAGTGGGCCTTACCCCAATCCATGTTGCTGC 315
 A  C  K  K  N  R  I  K  V  M  E  L  L  L  K  H  G  A  S  I  Q  A  V  T  E  S  G  L  T  P  I  H  V  A  A   62
                                                          · R3
CTTCATGGGGCATGTAAATATTGTATCACAACTAAGTGAGCCTCACCAAACACCACCAATGTGAGAGGAGAAACAGCACTGCACATGGCAGCTCGCTC    420
 F  M  G  H  V  N  I  V  S  Q  L  M  H  H  G  A  S  P  N  T  T  N  V  R  G  E  T  A  L  H  M  A  A  R  S   97
                                                          · R4
CGGCCAAGCTGAAGTTGTGCGGTATCTGGTACAAGACGAGCTCAGGTAGAAGCTAAAGCTAAAGCAAAAGACGATGACCAAACTTCAGCCCGACTGGGGAA 525
 G  Q  A  E  V  V  R  Y  L  V  Q  D  G  A  Q  V  E  A  K  D  D  Q  T  P  L  H  I  S  A  R  L  G  K       132
                                                          · R5
AGCAGACATAGTACAACAGCTGTGCAGCAGCTCTCGGTACACCTCTGGTACACTTCTGGTACACTGGCCAGCAAAATATGAAAGCTTGAAGTGC        630
 A  D  I  V  Q  Q  L  L  Q  Q  G  A  S  P  N  A  A  T  T  S  G  Y  T  P  L  H  L  S  A  R  E  G  H  E  D 167
                                                          · R6
TGTGGCCCGGTTCCTTTTGGATCATGGAGCGTCTTTATCTATAACAACAAAGAATTACTCCTCTTCATGTGGCAGCAAAATATGAAAGCTTGAAGTGC   735
 V  A  A  F  L  L  D  H  G  A  S  L  S  I  T  T  K  K  G  F  T  P  L  H  V  A  A  K  Y  G  K  L  E  V  A 202
                                                          · R7
CAATCTCCTGCTACAGAAAATGCATCTCCAGATGCTGCGGAAGAAGCTAACGATGCTCATGTAGCTGCACATTACGATAATCAGAAAGTGGCCCTTCT   840
 N  L  L  Q  K  S  A  S  P  D  A  A  G  K  S  G  L  T  P  L  H  V  A  A  H  Y  D  N  Q  K  V  A  L  L     237
                                                          · R8
GCTTTTTGACCAAGGAGCCTCACCTCACGCGCAGCCGCAAAGAATGGTTATACGCCACTGCACATGCTCACATGATAGCCACAACTCTGCT          945
 L  L  D  Q  G  A  S  P  H  A  A  A  K  N  G  Y  T  P  L  H  I  A  A  K  K  N  Q  M  D  I  A  T  T  L  L 272
                                                          · R9
GGAATATGGCTGATGCCAACGCAGTTACCCGGCAAGGAATTGCTTCCGTCCATCTCGCCAGTCAGGAGGGCCACGTGATGGTGTCGCTGCTCGGTAG    1050
 E  Y  G  A  D  A  N  A  V  T  R  Q  G  I  A  S  V  H  L  A  A  Q  E  G  H  V  D  M  V  S  L  L  G  R    307
                                                          · R10
AAATGCGAATGTGAACCTGAGCAATGAAAAGAGCGGCTTGACTCCACTGCATGCAGCAGAAGATCGAGTGAATGCTGTAAACCAAGGGC           1155
 N  A  N  V  N  L  S  N  K  S  G  L  T  P  L  H  L  A  A  Q  E  D  R  V  N  V  A  E  V  L  V  N  Q  G  A 342
                                                          · R11
TCATGTGGACGCCCAGACAAAGATGGGATACACCACTGCATGTGGGCTGCACTATGGGCAATATAGAAATATCAGAATTGTTAATTCCTGCTCCAGCATTCTGCAAAAGT 1260
 H  V  D  A  Q  T  K  M  G  Y  T  P  L  H  V  G  C  H  Y  G  N  I  K  I  V  N  F  L  L  Q  H  S  A  K  V  377
```

FIG. 2b

```
                                                                                              1365
•R12
TAATGCCAAAACAAAGAATGGGTATACGCCATTACATCAAGCAGCACAGAGGGGCATACGCAGCATATAATAAATGTCTTACTTCAGAACAACGCTCCCCAATGA
 N  A  K  T  K  N  G  Y  T  P  L  H  Q  A  A  Q  Q  G  H  T  H  I  I  N  V  L  L  Q  N  N  A  S  P  N  E    412
•R13
ACTCACTGTGAATGGGAATACTGCCCTTGGCATTGCCCGGGCGCTCGGCTACATCTCAGTAGTGGACACCCTGAAGATAGTGACCGAAGAACCATGACCACAAC  1470
 L  T  V  N  G  N  T  A  L  G  I  A  R  R  L  G  Y  I  S  V  V  D  T  L  K  I  V  T  E  E  T  M  T  T  T    447
•spectrin binding domain starts
TACTGTCACAGAGAAGCACACAAAATGAATGTTCCAGAAACATGATGAGTTCTTGATATGTCTGATGATGAAGGTGAAGATGAATGACCGGGACAATGAGACAA  1575
 T  V  T  E  K  H  H  K  M  N  V  P  E  T  M  N  E  V  L  D  M  S  D  D  E  G  E  D  A  M  T  G  D  T  D  K  482
ATATCTTGGGCCACACGGACCTTAAGGAATTGGGTGATGATTCCCTGCCTGCAGAGGGTTACATGGGCTTTAGTCTGGAGCGGTTCTGCCAGCGATAGGTCTTA  1680
 Y  L  G  P  Q  D  L  K  E  L  G  D  D  S  L  P  A  E  G  Y  M  G  F  S  L  G  A  R  S  A  S  D  R  S  Y    517
CACCTTGAACAGAAGCTCCTATGCACGGGACATGAGTATGATTGAAGAACTCCTTGTCCATCCAAAGAGCATCTAACATTCACAAGGAATTGATTCAGA      1785
 T  L  N  R  S  S  Y  A  R  D  S  M  M  I  E  E  L  L  V  P  S  K  E  Q  H  L  T  F  T  R  E  F  D  S  D    552
TTCTCTTAGACATTACAGCTGGCTGCAGACACCTTAGACAATGTCAATCTTGTTTCAAGCCCCATTCATTCTGGTTCTCGGTTAGCTTTATGGTGACGCGGAG  1890
 S  L  R  H  Y  S  W  A  A  D  T  L  D  N  V  N  L  V  S  S  P  I  H  S  G  F  L  V  S  F  M  V  D  A  R    587
AGGGGGGCTCCATGAGAGGAAGCCGTCATCACGGGATGAGAATCATCATCCCCACGCAAGTGTACGGCCCCACTGCAATCACTGCCGTTGTGGTAAAGAGACA  1995
 G  G  S  M  R  G  S  R  H  H  G  M  R  I  I  I  P  P  R  K  C  T  A  P  T  R  I  T  C  R  L  V  K  R  H    622
TAAAACTGGCCAACCACCCCCACATGGTGAAGAGAGGGATTAGCAGTAGGCTCCTGCAGGGGCACACAATTTTTAGGCCCTGTCATAGTGA              2100
 K  L  A  N  P  P  P  H  G  E  R  R  G  I  S  S  R  L  V  E  M  G  P  A  G  A  Q  F  L  G  P  V  I  V  E    657
AATCCCTCACTTTGGGTCCATGAGACGGGGGAAAGAGAGAACTCATTGTCTTCTCGAAGTGAAACTTGAAGGAGCATCAGTTGACACAGCAAAATGA          2205
 I  P  H  F  G  S  M  R  G  K  E  R  E  L  I  V  L  R  S  E  N  G  E  T  W  K  E  H  Q  F  D  S  K  N  E    692
AGAGTTAACGAGTTACTTAATGGCATGGATGAAGAACTTGATAGCCCAGAAGAGTTAGGGAAAAAGTTAGGGAAAAAGGTATCTGCAGGATTATCACGAAAGATTCCCCAGTA  2310
 D  L  T  E  L  L  N  G  M  D  E  E  L  D  S  P  E  E  L  G  K  K  R  I  C  R  I  I  T  K  D  F  P  Q  Y    727
```

FIG. 2c

```
TTTTGCAGTGGTTCCCGGATTAAGCAGGAAAGCAACCAGATTGGTCCTGAAGGTGGAATTCTGAGCAGCACCACAGTGCCCCTTGTTCAAGCATCTTTCCAGA  2415
 F  A  V  V  S  R  I  K  Q  E  S  N  Q  I  G  P  E  G  G  I  L  S  S  T  T  V  P  L  V  Q  A  S  F  P  E   762

GGGTGCCCTAACTAAAAGAATTCGAGTGGGCCTCCAGGCCCAGCCTGTTCCAGATGAAATTGTGAAAAAGATCCTTGGAAACAACAACTTTAGCCCAATTGT  2520
 G  A  L  T  K  R  I  R  V  G  L  Q  A  Q  P  V  P  D  E  I  V  K  K  I  L  G  N  K  A  T  F  S  P  I  V   797

CACTGTGGAACCAAGAAGACGAAAATTCATAAACCATCACAATGACCATTCCGGTGCCCCCCCCTCAGGAGAAGTGTATCAATGGATACAAGGGGACAC    2625
 T  V  E  P  R  R  K  F  H  K  P  I  T  M  T  I  P  V  P  P  P  S  G  E  G  V  S  N  G  Y  K  G  D  T    832

TACACCCAATCTGCGTCTTCTCTGTAGCATTACAGGGGGCCACTCCGCCCCTCAGTGGGAAGACATCACAGGAACAACTCCTTTGACGTTTATAAAAGATTGT  2730
 T  P  N  L  R  L  L  C  S  I  T  G  G  T  S  P  A  Q  W  E  D  I  T  G  T  T  P  L  T  F  F  I  K  D  C  V  867

CTCCTTTACAACCAACTGTTCAGCCAGATTTTGGCTTGCAGACTGCCATCAAGTTTAGAAACTGTGGGGTTAGCCACGACTGTACAGAATGATATGT  2835
 S  F  T  T  N  V  S  A  R  F  W  L  A  D  C  H  Q  V  L  E  T  V  G  L  A  T  Q  L  Y  R  E  L  I  C  V   902

TCCATATATGGCCAAGTTTGTTGTTTTGCCAAAATGAATGATCCCGTAGAATCTTCCTTGCGATGTTCTGCATGACAGATGACAAAGTGGACAAAACTTTAGA  2940
 P  Y  M  A  K  F  V  V  F  A  K  M  N  D  P  V  E  S  S  L  R  C  F  C  M  T  D  D  K  V  D  K  T  L  E   937

GCAACAAGAGAGCAACTTGAGAAGGTGCAAGAAGCAAAGATATTGAGGTTCTGGAAGGAAAAACCTATTTATGTTGATTGTTATGGAAATTTGGCCCCACTTACCAA  3045
 Q  Q  E  N  F  E  E  V  A  R  S  K  D  I  E  V  L  E  G  K  P  I  Y  V  D  C  Y  G  N  L  A  P  L  T  K   972

AGGAGGACAGCAACTTGTTTTAACTTTTATTCTTTCAAAGAAAATAGACTGCCATTTCCATCAAGATTAGAGACACCAGCCAAGAGCCCTGTGGTCGTCTC  3150
 G  G  Q  Q  L  V  F  N  F  Y  S  F  K  E  N  R  L  P  F  S  I  K  I  R  D  T  S  Q  E  P  C  G  R  L  S  1007

TTTTCTGAAAGAACCAAAGAACAACAAAAGGACTGCCTCAAACAGCGGTTTGCAACTTAAATCACTCTGCCAGCACATAAAAAGATTGAGAAACAGATAGACG  3255
 F  L  K  E  P  K  T  T  K  G  L  P  Q  T  A  V  C  N  L  N  I  T  L  P  A  H  K  K  I  E  K  T  D  R  R  1042

ACAGAGCTTCGCATCCTTAGCTTTACGTAAGGCTACTCAGCGCTACTGAGTGAGTTCCTGAGCCTGAATGAGTGAGGCCTGAATCGGGTCAATGTTTTAG    3360
 Q  S  F  A  S  L  R  K  R  Y  S  V  L  T  E  P  G  M  S  E  F  P  D  T  S  T  N  P  G  Q  C  F  R  1077

GAGAAGAGACATTTTTCTATGCGCTCTAAATTATGATGTGTTTCGAAAATAAACGCCCTGGGCCAAAAAAAAAAAAAAAAAAA             3454
 R  R  D  I  F  S  M  R  S  K  L  *                                                                 1089
```

· regulatory domain starts

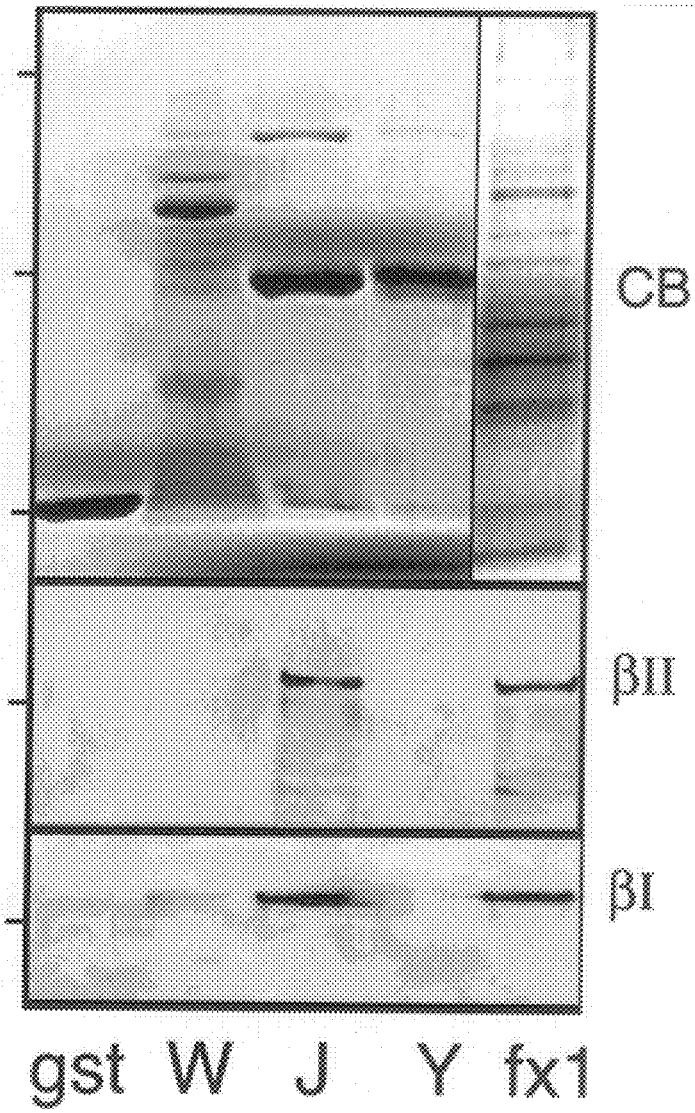

SEQUENCE LISTING

<160> NUMBER OF SEQ ID NOS: 19

<210> SEQ ID NO 1
<211> LENGTH: 3454
<212> TYPE: DNA
<213> ORGANISM: Homo sapiens
<220> FEATURE:
<221> NAME/KEY: CDS
<222> LOCATION: (131)..(3394)
<223> OTHER INFORMATION: DNA/protein segment- human kidney Ankyrin G119

<400> SEQUENCE: 1

```
ggagctcttc tcactcaagc ccgagtttct atgttcagac atagtacatt catcactgtg      60
tccttccagg atttggaagt ctgacaaaac accattccag tagctgcatc tccaggtttt     120
gagtctagaa atg aat tta aga tgt gat ctc ttg gat aag aaa gct aac        169
         Met Asn Leu Arg Cys Asp Leu Leu Asp Lys Lys Ala Asn
           1               5                  10 ccc aat gcc aaa gcc ctg aat ggc ttt acc cct ctt cat att gcc tgc       217
Pro Asn Ala Lys Ala Leu Asn Gly Phe Thr Pro Leu His Ile Ala Cys
 15                  20                  25 aag aag aat cga att aaa gta atg gaa ctc ctt ctg aaa cac ggt gca       265
Lys Lys Asn Arg Ile Lys Val Met Glu Leu Leu Leu Lys His Gly Ala
 30                  35                  40                  45 tcc atc caa gct gta acc gag tcg ggc ctt acc cca atc cat gtt gct       313
Ser Ile Gln Ala Val Thr Glu Ser Gly Leu Thr Pro Ile His Val Ala
                 50                  55                  60 gcc ttc atg ggg cat gta aat att gta tca caa cta atg cat cat gga       361
Ala Phe Met Gly His Val Asn Ile Val Ser Gln Leu Met His His Gly
         65                  70                  75 gcc tca cca aac acc acc aat gtg aga gga gaa aca gca ctg cac atg       409
Ala Ser Pro Asn Thr Thr Asn Val Arg Gly Glu Thr Ala Leu His Met
     80                  85                  90
```

```
gca gct cgc tcc ggc caa gct gaa gtt gtg cgg tat ctg gta caa gac      457
Ala Ala Arg Ser Gly Gln Ala Glu Val Val Arg Tyr Leu Val Gln Asp
         95                 100                 105 gga gct cag gta gaa gct aaa gct aag gat gac caa aca cca ctc cac      505
Gly Ala Gln Val Glu Ala Lys Ala Lys Asp Asp Gln Thr Pro Leu His
110                 115                 120                 125 att tca gcc cga ctg ggg aaa gca gac ata gta caa cag ctg ttg cag      553
Ile Ser Ala Arg Leu Gly Lys Ala Asp Ile Val Gln Gln Leu Leu Gln
                130                 135                 140 caa ggg gca tct cca aat gca gcc aca act tct ggg tac acc cca ctt      601
Gln Gly Ala Ser Pro Asn Ala Ala Thr Thr Ser Gly Tyr Thr Pro Leu
            145                 150                 155 cac ctt tcc gcc cga gag ggg cat gag gat gtg gcc gcg ttc ctt ttg      649
His Leu Ser Ala Arg Glu Gly His Glu Asp Val Ala Ala Phe Leu Leu
        160                 165                 170 gat cat gga gcg tct tta tct ata aca aca aag aaa gga ttt act cct      697
Asp His Gly Ala Ser Leu Ser Ile Thr Thr Lys Lys Gly Phe Thr Pro
    175                 180                 185 ctt cat gtg gca gca aaa tat gga aag ctt gaa gtc gcc aat ctc ctg      745
Leu His Val Ala Ala Lys Tyr Gly Lys Leu Glu Val Ala Asn Leu Leu
190                 195                 200                 205 cta cag aaa agt gca tct cca gat gct gct ggg aag agc ggg cta aca      793
Leu Gln Lys Ser Ala Ser Pro Asp Ala Ala Gly Lys Ser Gly Leu Thr
                210                 215                 220 cca ctg cat gta gct gca cat tac gat aat cag aaa gtg gcc ctt ctg      841
Pro Leu His Val Ala Ala His Tyr Asp Asn Gln Lys Val Ala Leu Leu
            225                 230                 235 ctt ttg gac caa gga gcc tca cct cac gca gcc gca aag aat ggt tat      889
Leu Leu Asp Gln Gly Ala Ser Pro His Ala Ala Ala Lys Asn Gly Tyr
        240                 245                 250 acg cca ctg cac atc gct gcc aaa aag aac cag atg gac ata gcg aca      937
Thr Pro Leu His Ile Ala Ala Lys Lys Asn Gln Met Asp Ile Ala Thr
    255                 260                 265 act ctg ctg gaa tat ggt gct gat gcc aac gca gtt acc cgg caa gga      985
Thr Leu Leu Glu Tyr Gly Ala Asp Ala Asn Ala Val Thr Arg Gln Gly
270                 275                 280                 285 att gct tcc gtc cat ctc gca gct cag gaa ggg cac gtg gac atg gtg     1033
Ile Ala Ser Val His Leu Ala Ala Gln Glu Gly His Val Asp Met Val
                290                 295                 300 tcg ctg ctc ctc ggt aga aat gcg aat gtg aac ctg agc aat aag agc     1081
Ser Leu Leu Leu Gly Arg Asn Ala Asn Val Asn Leu Ser Asn Lys Ser
            305                 310                 315 ggc ctg acc cca ctc cat ttg gct gct caa gaa gat cga gtg aat gtg     1129
Gly Leu Thr Pro Leu His Leu Ala Ala Gln Glu Asp Arg Val Asn Val
        320                 325                 330 gca gaa gtc ctc gta aac caa ggg gct cat gtg gac gcc cag aca aag     1177
Ala Glu Val Leu Val Asn Gln Gly Ala His Val Asp Ala Gln Thr Lys
    335                 340                 345 atg gga tac aca cca ctg cat gtg ggc tgc cac tat gga aat atc aag     1225
Met Gly Tyr Thr Pro Leu His Val Gly Cys His Tyr Gly Asn Ile Lys
350                 355                 360                 365 att gtt aat ttc ctg ctc cag cat tct gca aaa gtt aat gcc aaa aca     1273
Ile Val Asn Phe Leu Leu Gln His Ser Ala Lys Val Asn Ala Lys Thr
                370                 375                 380 aag aat ggg tat acg cca tta cat caa gca gca cag cag ggg cat acg     1321
Lys Asn Gly Tyr Thr Pro Leu His Gln Ala Ala Gln Gln Gly His Thr
            385                 390                 395 cat ata ata aat gtc tta ctt cag aac aac gcc tcc ccc aat gaa ctc     1369
His Ile Ile Asn Val Leu Leu Gln Asn Asn Ala Ser Pro Asn Glu Leu
```

```
                400                  405                  410
act gtg aat ggg aat act gcc ctt ggc att gcc cgg cgg ctc ggc tac    1417
Thr Val Asn Gly Asn Thr Ala Leu Gly Ile Ala Arg Arg Leu Gly Tyr
        415                  420                  425 atc tca gta gtg gac acc ctg aag ata gtg acc gaa gaa acc atg acc    1465
Ile Ser Val Val Asp Thr Leu Lys Ile Val Thr Glu Glu Thr Met Thr
430                  435                  440                  445 aca act act gtc aca gag aag cac aaa atg aat gtt cca gaa acg atg    1513
Thr Thr Thr Val Thr Glu Lys His Lys Met Asn Val Pro Glu Thr Met
                450                  455                  460 aat gaa gtt ctt gat atg tct gat gat gaa ggt gaa gat gca atg acc    1561
Asn Glu Val Leu Asp Met Ser Asp Asp Glu Gly Glu Asp Ala Met Thr
            465                  470                  475 ggg gac aca gac aaa tat ctt ggg cca cag gac ctt aag gaa ttg ggt    1609
Gly Asp Thr Asp Lys Tyr Leu Gly Pro Gln Asp Leu Lys Glu Leu Gly
        480                  485                  490 gat gat tcc ctg cct gca gag ggt tac atg ggc ttt agt ctc gga gcg    1657
Asp Asp Ser Leu Pro Ala Glu Gly Tyr Met Gly Phe Ser Leu Gly Ala
    495                  500                  505 cgt tct gcc agc gat agg tct tac acc ttg aac aga agc tcc tat gca    1705
Arg Ser Ala Ser Asp Arg Ser Tyr Thr Leu Asn Arg Ser Ser Tyr Ala
510                  515                  520                  525 cgg gac agc atg atg att gaa gaa ctc ctt gtg cca tcc aaa gag cag    1753
Arg Asp Ser Met Met Ile Glu Glu Leu Leu Val Pro Ser Lys Glu Gln
                530                  535                  540 cat cta aca ttc aca agg gaa ttt gat tca gat tct ctt aga cat tac    1801
His Leu Thr Phe Thr Arg Glu Phe Asp Ser Asp Ser Leu Arg His Tyr
            545                  550                  555 agc tgg gct gca gac acc tta gac aat gtc aat ctt gtt tca agc ccc    1849
Ser Trp Ala Ala Asp Thr Leu Asp Asn Val Asn Leu Val Ser Ser Pro
        560                  565                  570 att cat tct ggg ttt ctg gtt agc ttt atg gtg gac gcg aga ggg ggc    1897
Ile His Ser Gly Phe Leu Val Ser Phe Met Val Asp Ala Arg Gly Gly
    575                  580                  585 tcc atg aga gga agc cgt cat cac ggg atg aga atc atc att cct cca    1945
Ser Met Arg Gly Ser Arg His His Gly Met Arg Ile Ile Ile Pro Pro
590                  595                  600                  605 cgc aag tgt acg gcc ccc act cga atc acc tgc cgt ttg gta aag aga    1993
Arg Lys Cys Thr Ala Pro Thr Arg Ile Thr Cys Arg Leu Val Lys Arg
                610                  615                  620 cat aaa ctg gcc aac cca ccc cca cat ggt gaa agg aga ggg att agc    2041
His Lys Leu Ala Asn Pro Pro Pro His Gly Glu Arg Arg Gly Ile Ser
            625                  630                  635 agt agg ctg gta gaa atg ggt cct gca ggg gca caa ttt tta ggc cct    2089
Ser Arg Leu Val Glu Met Gly Pro Ala Gly Ala Gln Phe Leu Gly Pro
        640                  645                  650 gtc ata gtg gaa atc cct cac ttt ggg tcc atg aga gga aaa gag aga    2137
Val Ile Val Glu Ile Pro His Phe Gly Ser Met Arg Gly Lys Glu Arg
    655                  660                  665 gaa ctc att gtt ctt cga agt gaa aat ggt gaa act tgg aag gag cat    2185
Glu Leu Ile Val Leu Arg Ser Glu Asn Gly Glu Thr Trp Lys Glu His
670                  675                  680                  685 cag ttt gac agc aaa aat gaa gat tta acc gag tta ctt aat ggc atg    2233
Gln Phe Asp Ser Lys Asn Glu Asp Leu Thr Glu Leu Leu Asn Gly Met
                690                  695                  700 gat gaa gaa ctt gat agc cca gaa gag tta ggg aaa aag cgt atc tgc    2281
Asp Glu Glu Leu Asp Ser Pro Glu Glu Leu Gly Lys Lys Arg Ile Cys
            705                  710                  715 agg att atc acg aaa gat ttc ccc cag tat ttt gca gtg gtt tcc cgg    2329
```

-continued

```
                    Arg Ile Ile Thr Lys Asp Phe Pro Gln Tyr Phe Ala Val Val Ser Arg
                                    720                 725                 730 att aag cag gaa agc aac cag att ggt cct gaa ggt gga att ctg agc                   2377
Ile Lys Gln Glu Ser Asn Gln Ile Gly Pro Glu Gly Gly Ile Leu Ser
735                 740                 745 agc acc aca gtg ccc ctt gtt caa gca tct ttc cca gag ggt gcc cta                   2425
Ser Thr Thr Val Pro Leu Val Gln Ala Ser Phe Pro Glu Gly Ala Leu
750                 755                 760                 765 act aaa aga att cga gtg ggc ctc cag gcc cag cct gtt cca gat gaa                   2473
Thr Lys Arg Ile Arg Val Gly Leu Gln Ala Gln Pro Val Pro Asp Glu
                770                 775                 780 att gtg aaa aag atc ctt gga aac aaa gca act ttt agc cca att gtc                   2521
Ile Val Lys Lys Ile Leu Gly Asn Lys Ala Thr Phe Ser Pro Ile Val
                785                 790                 795 act gtg gaa cca aga aga cgg aaa ttc cat aaa cca atc aca atg acc                   2569
Thr Val Glu Pro Arg Arg Arg Lys Phe His Lys Pro Ile Thr Met Thr
800                 805                 810 att ccg gtg ccc ccg ccc tca gga gaa ggt gta tcc aat gga tac aaa                   2617
Ile Pro Val Pro Pro Pro Ser Gly Glu Gly Val Ser Asn Gly Tyr Lys
815                 820                 825 ggg gac act aca ccc aat ctg cgt ctt ctc tgt agc att aca ggg ggc                   2665
Gly Asp Thr Thr Pro Asn Leu Arg Leu Leu Cys Ser Ile Thr Gly Gly
830                 835                 840                 845 act tcg cct gct cag tgg gaa gac atc aca gga aca act cct ttg acg                   2713
Thr Ser Pro Ala Gln Trp Glu Asp Ile Thr Gly Thr Thr Pro Leu Thr
                850                 855                 860 ttt ata aaa gat tgt gtc tcc ttt aca acc aat gtt tca gcc aga ttt                   2761
Phe Ile Lys Asp Cys Val Ser Phe Thr Thr Asn Val Ser Ala Arg Phe
                865                 870                 875 tgg ctt gca gac tgc cat caa gtt tta gaa act gtg ggg tta gcc acg                   2809
Trp Leu Ala Asp Cys His Gln Val Leu Glu Thr Val Gly Leu Ala Thr
                880                 885                 890 caa ctg tac aga gaa ttg ata tgt gtt cca tat atg gcc aag ttt gtt                   2857
Gln Leu Tyr Arg Glu Leu Ile Cys Val Pro Tyr Met Ala Lys Phe Val
895                 900                 905 gtt ttt gcc aaa atg aat gat ccc gta gaa tct tcc ttg cga tgt ttc                   2905
Val Phe Ala Lys Met Asn Asp Pro Val Glu Ser Ser Leu Arg Cys Phe
910                 915                 920                 925 tgc atg aca gat gac aaa gtg gac aaa act tta gag caa caa gag aat                   2953
Cys Met Thr Asp Asp Lys Val Asp Lys Thr Leu Glu Gln Gln Glu Asn
                930                 935                 940 ttt gag gaa gtc gca aga agc aaa gat att gag gtt ctg gaa gga aaa                   3001
Phe Glu Glu Val Ala Arg Ser Lys Asp Ile Glu Val Leu Glu Gly Lys
                945                 950                 955 cct att tat gtt gat tgt tat gga aat ttg gcc cca ctt acc aaa gga                   3049
Pro Ile Tyr Val Asp Cys Tyr Gly Asn Leu Ala Pro Leu Thr Lys Gly
                960                 965                 970 gga cag caa ctt gtt ttt aac ttt tat tct ttc aaa gaa aat aga ctg                   3097
Gly Gln Gln Leu Val Phe Asn Phe Tyr Ser Phe Lys Glu Asn Arg Leu
975                 980                 985 cca ttt tcc atc aag att aga gac acc agc caa gag ccc tgt ggt cgt                   3145
Pro Phe Ser Ile Lys Ile Arg Asp Thr Ser Gln Glu Pro Cys Gly Arg
990                 995                 1000                1005 ctg tct ttt ctg aaa gaa cca aag aca aca aaa gga ctg cct caa aca                   3193
Leu Ser Phe Leu Lys Glu Pro Lys Thr Thr Lys Gly Leu Pro Gln Thr
                1010                1015                1020 gcg gtt tgc aac tta aat atc act ctg cca gca cat aaa aag att gag                   3241
Ala Val Cys Asn Leu Asn Ile Thr Leu Pro Ala His Lys Lys Ile Glu
                1025                1030                1035
```

```
aaa aca gat aga cga cag agc ttc gca tcc tta gct tta cgt aag cgc    3289
Lys Thr Asp Arg Arg Gln Ser Phe Ala Ser Leu Ala Leu Arg Lys Arg
        1040                1045                1050 tac agc tac ttg act gag cct gga atg agt gag ttt cct gac acg tcc    3337
Tyr Ser Tyr Leu Thr Glu Pro Gly Met Ser Glu Phe Pro Asp Thr Ser
    1055                1060                1065 act aat ccg ggt caa tgt ttt agg aga aga gac att ttt tct atg cgc    3385
Thr Asn Pro Gly Gln Cys Phe Arg Arg Arg Asp Ile Phe Ser Met Arg
1070                1075                1080                1085 tct aaa tta tgatgtggtt tcgaaataa acgccctggg ccaaaaaaaa             3434
Ser Lys Leu aaaaaaaaaa aaaaaaaaa                                                3454

<210> SEQ ID NO 2
<211> LENGTH: 1088
<212> TYPE: PRT
<213> ORGANISM: Homo sapiens

<400> SEQUENCE: 2

Met Asn Leu Arg Cys Asp Leu Leu Asp Lys Lys Ala Asn Pro Asn Ala
  1               5                  10                  15

Lys Ala Leu Asn Gly Phe Thr Pro Leu His Ile Ala Cys Lys Lys Asn
                 20                  25                  30

Arg Ile Lys Val Met Glu Leu Leu Leu Lys His Gly Ala Ser Ile Gln
             35                  40                  45

Ala Val Thr Glu Ser Gly Leu Thr Pro Ile His Val Ala Ala Phe Met
         50                  55                  60

Gly His Val Asn Ile Val Ser Gln Leu Met His His Gly Ala Ser Pro
 65                  70                  75                  80

Asn Thr Thr Asn Val Arg Gly Glu Thr Ala Leu His Met Ala Ala Arg
                 85                  90                  95

Ser Gly Gln Ala Glu Val Val Arg Tyr Leu Val Gln Asp Gly Ala Gln
                100                 105                 110

Val Glu Ala Lys Ala Lys Asp Asp Gln Thr Pro Leu His Ile Ser Ala
            115                 120                 125

Arg Leu Gly Lys Ala Asp Ile Val Gln Gln Leu Leu Gln Gln Gly Ala
        130                 135                 140

Ser Pro Asn Ala Ala Thr Thr Ser Gly Tyr Thr Pro Leu His Leu Ser
145                 150                 155                 160

Ala Arg Glu Gly His Glu Asp Val Ala Ala Phe Leu Leu Asp His Gly
                165                 170                 175

Ala Ser Leu Ser Ile Thr Thr Lys Lys Gly Phe Thr Pro Leu His Val
            180                 185                 190

Ala Ala Lys Tyr Gly Lys Leu Glu Val Ala Asn Leu Leu Leu Gln Lys
        195                 200                 205

Ser Ala Ser Pro Asp Ala Ala Gly Lys Ser Gly Leu Thr Pro Leu His
    210                 215                 220

Val Ala His Tyr Asp Asn Gln Lys Val Ala Leu Leu Leu Leu Asp
225                 230                 235                 240

Gln Gly Ala Ser Pro His Ala Ala Ala Lys Asn Gly Tyr Thr Pro Leu
                245                 250                 255

His Ile Ala Ala Lys Lys Asn Gln Met Asp Ile Ala Thr Thr Leu Leu
            260                 265                 270

Glu Tyr Gly Ala Asp Ala Asn Ala Val Thr Arg Gln Gly Ile Ala Ser
        275                 280                 285
```

-continued

```
Val His Leu Ala Ala Gln Glu Gly His Val Asp Met Val Ser Leu Leu
    290                 295                 300
Leu Gly Arg Asn Ala Asn Val Asn Leu Ser Asn Lys Ser Gly Leu Thr
305                 310                 315                 320
Pro Leu His Leu Ala Ala Gln Glu Asp Arg Val Asn Val Ala Glu Val
                325                 330                 335
Leu Val Asn Gln Gly Ala His Val Asp Ala Gln Thr Lys Met Gly Tyr
                340                 345                 350
Thr Pro Leu His Val Gly Cys His Tyr Gly Asn Ile Lys Ile Val Asn
            355                 360                 365
Phe Leu Leu Gln His Ser Ala Lys Val Asn Ala Lys Thr Lys Asn Gly
370                 375                 380
Tyr Thr Pro Leu His Gln Ala Ala Gln Gln Gly His Thr His Ile Ile
385                 390                 395                 400
Asn Val Leu Leu Gln Asn Asn Ala Ser Pro Asn Glu Leu Thr Val Asn
                405                 410                 415
Gly Asn Thr Ala Leu Gly Ile Ala Arg Arg Leu Gly Tyr Ile Ser Val
                420                 425                 430
Val Asp Thr Leu Lys Ile Val Thr Glu Glu Thr Met Thr Thr Thr Thr
            435                 440                 445
Val Thr Glu Lys His Lys Met Asn Val Pro Glu Thr Met Asn Glu Val
        450                 455                 460
Leu Asp Met Ser Asp Asp Glu Gly Glu Asp Ala Met Thr Gly Asp Thr
465                 470                 475                 480
Asp Lys Tyr Leu Gly Pro Gln Asp Leu Lys Glu Leu Gly Asp Asp Ser
                485                 490                 495
Leu Pro Ala Glu Gly Tyr Met Gly Phe Ser Leu Gly Ala Arg Ser Ala
                500                 505                 510
Ser Asp Arg Ser Tyr Thr Leu Asn Arg Ser Ser Tyr Ala Arg Asp Ser
            515                 520                 525
Met Met Ile Glu Glu Leu Leu Val Pro Ser Lys Glu Gln His Leu Thr
530                 535                 540
Phe Thr Arg Glu Phe Asp Ser Asp Ser Leu Arg His Tyr Ser Trp Ala
545                 550                 555                 560
Ala Asp Thr Leu Asp Asn Val Asn Leu Val Ser Ser Pro Ile His Ser
                565                 570                 575
Gly Phe Leu Val Ser Phe Met Val Asp Ala Arg Gly Gly Ser Met Arg
                580                 585                 590
Gly Ser Arg His His Gly Met Arg Ile Ile Ile Pro Pro Arg Lys Cys
            595                 600                 605
Thr Ala Pro Thr Arg Ile Thr Cys Arg Leu Val Lys Arg His Lys Leu
610                 615                 620
Ala Asn Pro Pro His Gly Glu Arg Gly Ile Ser Ser Arg Leu
625                 630                 635                 640
Val Glu Met Gly Pro Ala Gly Ala Gln Phe Leu Gly Pro Val Ile Val
                645                 650                 655
Glu Ile Pro His Phe Gly Ser Met Arg Gly Lys Glu Arg Glu Leu Ile
                660                 665                 670
Val Leu Arg Ser Glu Asn Gly Glu Thr Trp Lys Glu His Gln Phe Asp
            675                 680                 685
Ser Lys Asn Glu Asp Leu Thr Glu Leu Leu Asn Gly Met Asp Glu Glu
690                 695                 700
Leu Asp Ser Pro Glu Glu Leu Gly Lys Lys Arg Ile Cys Arg Ile Ile
```

-continued

```
            705                 710                 715                 720
Thr Lys Asp Phe Pro Gln Tyr Phe Ala Val Val Ser Arg Ile Lys Gln
                725                 730                 735
Glu Ser Asn Gln Ile Gly Pro Glu Gly Gly Ile Leu Ser Ser Thr Thr
            740                 745                 750
Val Pro Leu Val Gln Ala Ser Phe Pro Glu Gly Ala Leu Thr Lys Arg
            755                 760                 765
Ile Arg Val Gly Leu Gln Ala Gln Pro Val Pro Asp Glu Ile Val Lys
            770                 775                 780
Lys Ile Leu Gly Asn Lys Ala Thr Phe Ser Pro Ile Val Thr Val Glu
785                 790                 795                 800
Pro Arg Arg Arg Lys Phe His Lys Pro Ile Thr Met Thr Ile Pro Val
                805                 810                 815
Pro Pro Pro Ser Gly Glu Gly Val Ser Asn Gly Tyr Lys Gly Asp Thr
            820                 825                 830
Thr Pro Asn Leu Arg Leu Leu Cys Ser Ile Thr Gly Gly Thr Ser Pro
            835                 840                 845
Ala Gln Trp Glu Asp Ile Thr Gly Thr Thr Pro Leu Thr Phe Ile Lys
            850                 855                 860
Asp Cys Val Ser Phe Thr Thr Asn Val Ser Ala Arg Phe Trp Leu Ala
865                 870                 875                 880
Asp Cys His Gln Val Leu Glu Thr Val Gly Leu Ala Thr Gln Leu Tyr
                885                 890                 895
Arg Glu Leu Ile Cys Val Pro Tyr Met Ala Lys Phe Val Val Phe Ala
                900                 905                 910
Lys Met Asn Asp Pro Val Glu Ser Ser Leu Arg Cys Phe Cys Met Thr
            915                 920                 925
Asp Asp Lys Val Asp Lys Thr Leu Glu Gln Gln Glu Asn Phe Glu Glu
            930                 935                 940
Val Ala Arg Ser Lys Asp Ile Glu Val Leu Glu Gly Lys Pro Ile Tyr
945                 950                 955                 960
Val Asp Cys Tyr Gly Asn Leu Ala Pro Leu Thr Lys Gly Gly Gln Gln
                965                 970                 975
Leu Val Phe Asn Phe Tyr Ser Phe Lys Glu Asn Arg Leu Pro Phe Ser
            980                 985                 990
Ile Lys Ile Arg Asp Thr Ser Gln Glu Pro Cys Gly Arg Leu Ser Phe
            995                 1000                1005
Leu Lys Glu Pro Lys Thr Thr Lys Gly Leu Pro Gln Thr Ala Val Cys
    1010                1015                1020
Asn Leu Asn Ile Thr Leu Pro Ala His Lys Lys Ile Glu Lys Thr Asp
1025                1030                1035                1040
Arg Arg Gln Ser Phe Ala Ser Leu Ala Leu Arg Lys Arg Tyr Ser Tyr
            1045                1050                1055
Leu Thr Glu Pro Gly Met Ser Glu Phe Pro Asp Thr Ser Thr Asn Pro
            1060                1065                1070
Gly Gln Cys Phe Arg Arg Arg Asp Ile Phe Ser Met Arg Ser Lys Leu
            1075                1080                1085

<210> SEQ ID NO 3
<211> LENGTH: 69
<212> TYPE: PRT
<213> ORGANISM: Homo sapiens
<220> FEATURE:
<223> OTHER INFORMATION: a.a. seq., Ank-B, human kidney cDNA library
```

```
<400> SEQUENCE: 3

Thr Thr Pro Leu Thr Phe Val Asn Glu Cys Val Ser Phe Thr Thr Asn
  1               5                  10                  15

Val Ser Ala Arg Phe Trp Leu Ile Asp Cys Arg Gln Ile Gln Glu Ser
             20                  25                  30

Val Thr Phe Ala Ser Gln Val Tyr Arg Glu Ile Ile Cys Val Pro Tyr
         35                  40                  45

Met Ala Lys Phe Val Val Phe Ala Lys Ser His Asp Pro Ile Glu Ala
     50                  55                  60

Arg Leu Arg Cys Phe
 65

<210> SEQ ID NO 4
<211> LENGTH: 69
<212> TYPE: PRT
<213> ORGANISM: Rattus
<220> FEATURE:
<223> OTHER INFORMATION: a.a. seq., Ank-B, rat kidney cDNA library

<400> SEQUENCE: 4

Thr Thr Pro Leu Thr Phe Val Asn Glu Cys Val Ser Phe Thr Thr Asn
  1               5                  10                  15

Val Ser Ala Arg Phe Trp Leu Ile Asp Cys Arg Gln Ile Gln Glu Ser
             20                  25                  30

Val Thr Phe Ala Ser Gln Val Tyr Phe Glu Ile Ile Cys Val Pro Tyr
         35                  40                  45

Met Ala Lys Phe Val Val Phe Ala Lys Ser His Asp Pro Ile Glu Ala
     50                  55                  60

Arg Leu Arg Cys Phe
 65

<210> SEQ ID NO 5
<211> LENGTH: 69
<212> TYPE: PRT
<213> ORGANISM: Rattus
<220> FEATURE:
<223> OTHER INFORMATION: a.a. seq., Ank-B, rev. transcribed rat kidney
      RNA

<400> SEQUENCE: 5

Thr Thr Pro Leu Thr Phe Val Asn Glu Cys Val Ser Phe Thr Thr Asn
  1               5                  10                  15

Val Ser Ala Arg Phe Trp Leu Ile Asp Cys Arg Gln Ile Gln Glu Ser
             20                  25                  30

Val Thr Phe Ala Ser Gln Val Tyr Phe Glu Ile Ile Cys Val Pro Tyr
         35                  40                  45

Met Ala Lys Phe Val Val Phe Ala Lys Ser His Asp Pro Ile Glu Ala
     50                  55                  60

Arg Leu Arg Cys Phe
 65

<210> SEQ ID NO 6
<211> LENGTH: 69
<212> TYPE: PRT
<213> ORGANISM: Canis
<220> FEATURE:
<223> OTHER INFORMATION: canine, a.a. seq., Ank-B, rev. transcribed MDCK
      cell RNA

<400> SEQUENCE: 6
```

```
Thr Thr Pro Leu Leu Tyr Val Asn Glu Cys Val Ser Phe Thr Thr Asn
 1               5                  10                  15

Val Ser Ala Arg Phe Trp Leu Ile Asp Cys Arg Gln Ile Gln Glu Ser
            20                  25                  30

Val Thr Phe Ala Ser Gln Val Tyr Phe Glu Ile Ile Cys Val Pro Tyr
                35                  40                  45

Met Ala Lys Phe Arg His Phe Ala Lys Ser His Asp Pro Ile Glu Ala
        50                  55                  60

Arg Val Arg Cys Tyr
 65

<210> SEQ ID NO 7
<211> LENGTH: 69
<212> TYPE: PRT
<213> ORGANISM: Porcus
<220> FEATURE:
<223> OTHER INFORMATION: porcine, a.a. seq., Ank-B, rev. transcribed
      LLC-PK1 cell RNA

<400> SEQUENCE: 7

Thr Thr Pro Leu Thr Phe Val Asn Glu Cys Val Ser Phe Thr Thr Asn
 1               5                  10                  15

Val Ser Ala Arg Phe Trp Leu Ile Asp Cys Arg Gln Ile Gln Glu Ser
            20                  25                  30

Val Thr Phe Ala Ser Gln Val Tyr Arg Glu Ile Ile Cys Val Pro Tyr
                35                  40                  45

Met Ala Lys Phe Val Val Phe Ala Lys Ser His Asp Pro Ile Glu Ala
        50                  55                  60

Arg Tyr Arg Cys Tyr
 65

<210> SEQ ID NO 8
<211> LENGTH: 69
<212> TYPE: PRT
<213> ORGANISM: Artificial Sequence
<220> FEATURE:
<221> NAME/KEY: variation
<222> LOCATION: (5), (6), (41), (53), (54), (66), (69)
<223> OTHER INFORMATION: consensus a.a. seq. related to Ank-B

<400> SEQUENCE: 8

Thr Thr Pro Leu Xaa Xaa Val Asn Glu Cys Val Ser Phe Thr Thr Asn
 1               5                  10                  15

Val Ser Ala Arg Phe Trp Leu Ile Asp Cys Arg Gln Ile Gln Glu Ser
            20                  25                  30

Val Thr Phe Ala Ser Gln Val Tyr Xaa Glu Ile Ile Cys Val Pro Tyr
                35                  40                  45

Met Ala Lys Phe Xaa Xaa Phe Ala Lys Ser His Asp Pro Ile Glu Ala
        50                  55                  60

Arg Xaa Arg Cys Xaa
 65

<210> SEQ ID NO 9
<211> LENGTH: 69
<212> TYPE: PRT
<213> ORGANISM: Homo sapiens
<220> FEATURE:
<223> OTHER INFORMATION: a.a. seq., Ank-G119, human kidney cDNA lib.

<400> SEQUENCE: 9

Thr Thr Pro Leu Thr Phe Ile Lys Asp Cys Val Ser Phe Thr Thr Asn
```

```
                1               5                  10                  15
Val Ser Ala Arg Phe Trp Leu Ala Asp Cys His Gln Val Leu Glu Thr
                    20                  25                  30

Val Gly Leu Ala Phe Gly Val Tyr Arg Glu Phe Ile Cys Val Pro Tyr
            35                  40                  45

Met Ala Lys Phe Val Val Phe Ala Lys Thr Asn His Pro Val Glu Phe
        50                  55                  60

Phe Leu Ser Asp Leu
 65

<210> SEQ ID NO 10
<211> LENGTH: 69
<212> TYPE: PRT
<213> ORGANISM: Rattus
<220> FEATURE:
<223> OTHER INFORMATION: a.a. seq., Ank-G119, rat kidney cDNA lib.

<400> SEQUENCE: 10

Thr Thr Pro Leu Thr Phe Ile Lys Asp Cys Val Ser Phe Thr Thr Asn
 1               5                  10                  15

Val Ser Ala Arg Phe Trp Leu Ala Asp Cys His Gln Val Leu Glu Thr
                    20                  25                  30

Val Gly Phe Ala Leu Asn Leu Tyr Arg Glu Phe Ile Cys Val Pro Tyr
            35                  40                  45

Met Ala Lys Phe Val Val Phe Ala Lys Thr Asn Asp Pro Val Glu Ser
        50                  55                  60

Ser Leu Arg Tyr Phe
 65

<210> SEQ ID NO 11
<211> LENGTH: 69
<212> TYPE: PRT
<213> ORGANISM: Rattus
<220> FEATURE:
<223> OTHER INFORMATION: a.a. seq., Ank-G119, rev. transcribed rat
      kidney RNA

<400> SEQUENCE: 11

Thr Thr Pro Leu Thr Phe Ile Lys Asp Cys Val Ser Phe Thr Thr Asn
 1               5                  10                  15

Val Ser Ala Arg Phe Trp Leu Ala Asp Cys His Gln Val Leu Glu Thr
                    20                  25                  30

Val Gly Phe Ala Leu Asn Leu Tyr Arg Glu Phe Ile Cys Val Pro Tyr
            35                  40                  45

Met Ala Lys Phe Val Val Phe Ala Lys Thr Asn Asp Pro Val Glu Ser
        50                  55                  60

Ser Leu Arg Tyr Phe
 65

<210> SEQ ID NO 12
<211> LENGTH: 69
<212> TYPE: PRT
<213> ORGANISM: Canis
<220> FEATURE:
<223> OTHER INFORMATION: canine, a.a. seq., Ank-G119, rev. transcribed
      MDCK RNA

<400> SEQUENCE: 12

Thr Thr Pro Leu Thr Phe Ile Lys Asp Cys Val Ser Phe Thr Thr Asn
 1               5                  10                  15
```

```
Val Ser Ala Arg Phe Trp Leu Ala Asp Cys His Gln Val Leu Glu Thr
            20                  25                  30

Val Gly Leu Ala Thr Asn Leu Tyr Arg Glu Phe Ile Cys Val Pro Tyr
        35                  40                  45

Met Ala Lys Phe Val Val Phe Ala Lys Thr Asn His Pro Val Glu Ser
    50                  55                  60

Ser Leu Arg Cys Tyr
 65
```

```
<210> SEQ ID NO 13
<211> LENGTH: 69
<212> TYPE: PRT
<213> ORGANISM: Porcus
<220> FEATURE:
<223> OTHER INFORMATION: porcine, a.a. seq, Ank-G119, rev. transcribed
      LLC-PK1 RNA

<400> SEQUENCE: 13

Thr Thr Pro Leu Thr Phe Ile Lys Asp Cys Val Ser Phe Thr Thr Asn
 1               5                  10                  15

Val Ser Ala Arg Phe Trp Leu Ala Asp Cys His Gln Val Leu Glu Thr
            20                  25                  30

Val Gly Leu Ala Thr Gln Leu Tyr Arg Glu Phe Ile Cys Val Pro Tyr
        35                  40                  45

Met Ala Lys Phe Val Val Phe Ala Lys Thr Asn Asp Pro Val Glu Ser
    50                  55                  60

Ser Leu Arg Cys Phe
 65
```

```
<210> SEQ ID NO 14
<211> LENGTH: 69
<212> TYPE: PRT
<213> ORGANISM: Artificial Sequence
<220> FEATURE:
<221> NAME/KEY: variation
<222> LOCATION: (35), (37)..(39), (60), (64), (65), (67)..(69)
<223> OTHER INFORMATION: consensus a.a. seq. related to Ank-G119

<400> SEQUENCE: 14

Thr Thr Pro Leu Thr Phe Ile Lys Asp Cys Val Ser Phe Thr Thr Asn
 1               5                  10                  15

Val Ser Ala Arg Phe Trp Leu Ala Asp Cys His Gln Val Leu Glu Thr
            20                  25                  30

Val Gly Xaa Ala Xaa Xaa Xaa Tyr Arg Glu Phe Ile Cys Val Pro Tyr
        35                  40                  45

Met Ala Lys Phe Val Val Phe Ala Lys Thr Asn Xaa Pro Val Glu Xaa
    50                  55                  60

Xaa Leu Xaa Xaa Xaa
 65
```

```
<210> SEQ ID NO 15
<211> LENGTH: 69
<212> TYPE: PRT
<213> ORGANISM: Homo sapiens
<220> FEATURE:
<223> OTHER INFORMATION: human a.a. sequence of Ank-R, binding domain

<400> SEQUENCE: 15

Thr Thr Lys Leu Val Val Ala Asn Glu Cys Ala Asn Phe Thr Thr Asn
 1               5                  10                  15

Val Ser Ala Arg Phe Trp Leu Ser Asp Cys Pro Arg Thr Ala Glu Ala
```

```
                    20                  25                  30
Val Asn Phe Ala Thr Leu Leu Tyr Lys Glu Leu Thr Ala Val Pro Tyr
                35                  40                  45

Met Ala Lys Phe Val Val Phe Ala Lys Met Asn Asp Pro Arg Glu Gly
            50                  55                  60

Arg Leu Arg Cys Phe
 65

<210> SEQ ID NO 16
<211> LENGTH: 69
<212> TYPE: PRT
<213> ORGANISM: Homo sapiens
<220> FEATURE:
<221> NAME/KEY: unsure
<222> LOCATION: (1), (2), (4), (8)..(10), (13)..(23), (25), (26), (31),
<223> OTHER INFORMATION: human a.a. sequence of Ank-B, binding domain

<400> SEQUENCE: 16

Xaa Xaa Pro Xaa Thr Phe Val Xaa Xaa Xaa Val Ser Xaa Xaa Xaa Xaa
 1               5                  10                  15

Xaa Xaa Xaa Xaa Xaa Xaa Xaa Ile Xaa Xaa Arg Gln Ile Gln Xaa Ser
                20                  25                  30

Xaa Thr Xaa Xaa Ser Gln Val Xaa Arg Xaa Ile Ile Cys Xaa Xaa Xaa
            35                  40                  45

Xaa Xaa Xaa Xaa Xaa Xaa Xaa Xaa Xaa Ser His Xaa Xaa Ile Xaa Ala
        50                  55                  60

Xaa Xaa Xaa Xaa Xaa
 65

<210> SEQ ID NO 17
<211> LENGTH: 69
<212> TYPE: PRT
<213> ORGANISM: Homo sapiens
<220> FEATURE:
<221> NAME/KEY: unsure
<222> LOCATION: (1), (2), (4), (10), (13)..(23), (25), (26), (31), (33),
<223> OTHER INFORMATION: human a.a. seq. of Ank-G119, binding domain

<400> SEQUENCE: 17

Xaa Xaa Pro Xaa Thr Phe Ile Lys Asp Xaa Val Ser Xaa Xaa Xaa Xaa
 1               5                  10                  15

Xaa Xaa Xaa Xaa Xaa Xaa Xaa Ala Xaa Xaa His Gln Val Leu Xaa Thr
                20                  25                  30

Xaa Gly Leu Xaa Phe Gly Val Xaa Arg Xaa Phe Ile Cys Xaa Xaa Xaa
            35                  40                  45

Xaa Xaa Xaa Xaa Xaa Xaa Xaa Xaa Xaa Thr Asn His Xaa Val Xaa Phe
        50                  55                  60

Phe Xaa Xaa Asp Leu
 65

<210> SEQ ID NO 18
<211> LENGTH: 23
<212> TYPE: DNA
<213> ORGANISM: Artificial Sequence
<220> FEATURE:
<223> OTHER INFORMATION: sense primer

<400> SEQUENCE: 18
gcccagtggg aagacataac agg                                        23

<210> SEQ ID NO 19
```

```
<211> LENGTH: 27
<212> TYPE: DNA
<213> ORGANISM: Artificial Sequence
<220> FEATURE:
<223> OTHER INFORMATION: anti-sense primer

<400> SEQUENCE: 19
cttgtccact tatcatctgt catgcag                                         27
```

POLYNUCLEOTIDES ENCODING ANKYRIN PROTEINS

This application claims priority of copending provisional application(s) No. 60/047,356 filed on May 21, 1997, which is herein incorporated by reference in its entirety.

ACKNOWLEDGMENT OF FEDERAL SUPPORT

The research and discoveries described herein were supported by grants from the National Institute of Diabetes and Kidney Disease: P01-DK38979, R01-DK43812 and R29-DK47072.

FIELD OF THE INVENTION

The present invention relates to novel ankyrin proteins and to methods for selectively identifying ankyrin proteins that participate in the trafficking of integral membrane proteins and secretory proteins between the endoplasmic reticulum and other membrane compartments. The present invention provides methods for identifying such ankyrin proteins and their various binding partners, such as spectrin, the binding domains responsible for spectrin-ankyrin binding, and the corresponding binding domains responsible for the binding of ankyrin to integral membrane or secretory proteins. The present invention also provides methods for identifying agents that modulate ankyrin binding and thereby enhance or inhibit the processing of integral membrane and secretory proteins.

BACKGROUND OF THE INVENTION

In all eukaryotic cells, a central and common process exists for integral membrane protein and secretory protein post-translational modification and delivery. This common process involves vesicular transport from their site of synthesis, the lumen of the rough endoplasmic reticulum (ER), to and through the Golgi apparatus, and ultimately to specific plasma membrane or internal membrane domains. See, e.g., Darnell et al., Molecular Cell Biology (1990, Scientific American Books) at Chapter 17, "Plasma-Membrane, Secretory, and Lysosome Proteins: Biosynthesis and Sorting."

Following protein synthesis in the ER, most proteins travel via small transport vesicles to the Golgi complex, an organelle composed of both flattened and spherical vesicles that serve as a liaison between the ER and both the plasma membrane and internal organelles, such as lysosomes. The Golgi complex contains three functional regions: (1) the elongated vesicles nearest the ER make up the cis face of the Golgi (2) those of the mid-portion, the medial face; and (3) those nearest the periphery of the cell, the trans face and the trans Golgi reticulum. Glycosylation is the principal chemical modification that occurs to proteins as they pass through the Golgi apparatus. See, e.g., Darnell et al., Molecular Cell Biology (1990, Scientific American Books) at Chapter 17, "Plasma-Membrane, Secretory, and Lysosome Proteins: Biosynthesis and Sorting."

The ankyrins are a family of proteins that mediate the linkage of the cytoskeleton to a variety of membrane transport and receptor proteins. Ankyrins are known to link the spectrin cytoskeleton and integral membrane proteins. Ankyrin has emerged as a ubiquitous protein linking integral membrane transport proteins such as Na,K-ATPase to an underlying spectrin cytoskeleton, Devarajan et al., PNAS: 2965–69 (1994). Multiple isoforms of ankyrin have arisen both by gene duplication as well as by alternative transcription, Devarajan et al., PNAS 91: 2965–69 (1994).

Spectrins and actin are the major components of a cell's cortical or membrane cytoskeleton. The membrane cytoskeleton is the major determinant of the rigidity of cell membranes and acts to restrict the lateral motion of membrane glycoproteins. The major constituents of the cytoskeleton are α- and β-spectrin and actin. Spectrin binds to the sides of actin microfilaments producing the lace-like cytoskeleton. Darnell et al., Molecular Cell Biology (1990, Scientific American Books) at Chapter 13, "The Plasma Membrane."

A. Ankyrins

Interactions between integral membrane proteins and the underlying spectrin-actin cytoskeleton play key roles in such activities as cell motility, activation, proliferation, contact, and the maintenance of specialized membrane domains (Luna and Hitt, Science 258: 955–64 (1992); Bennett and Gilligan, Annu. Rev. Cell Biol. 9: 27–66 (1993); Devarajan and Morrow, Membrane Protein-Cytoskeleton Complexes: Protein Interactions, Distributions and Functions (1996, Academic Press); Morrow et al., Handbook of Physiology (1997, Oxford Press). Ankyrins are a family of large membrane associated proteins that have emerged as crucial adapter molecules mediating such linkages, since they possess recognition sites for various membrane proteins as well as for cytoskeletal elements, Bennett, J. Biol. Chem. 267: 8703–6 (1992). Molecules employing a 33 residue repetitive structure first identified in the 89 kDa domain I of ankyrin display a wide tissue distribution. Bork, Proteins 17: 363–74 (1993); Chan et al., J. Cell Biol. 123: 1463–73 (1993); Axton et al., EMBO. J. 13: 462–70 (1994); Diederich et al., Develop. 120: 473–81 (1994), and tissue-specific isoforms may be present in all cells (Lux et al., Nature 344: 36–42 (1990a).

Several distinct isoforms of ankyrin have been recognized by their immunological properties. The isoform associated with the membranes of red cells, neuronal cell bodies and dendrites has been termed $Ank_R$. Antibodies to $Ank_R$ also cross-react with an ankyrin found in the basolateral membrane of polarized epithelial cells. Davis et al., J. Biol., Chem. 264: 6417–26 (1989); Morrow et al., J. Cell Biol. 108: 455–65 (1989)). $Ank_R$ is encoded by the ANK1 gene (Lux et al., (1990a); Lux et al., Nature 345: 736–39 (1990b)), which transcribes mRNA species of 7 kilobases (Kb) in erythrocytes (Lambert et al., 1990; Lux et al., Nature 344: 36–42 (1990a)) and 9 Kb in brain (Lambert et al., 1990).

$Ank_B$ is the major isoform in brain, and is widely present in neuronal and glial cell membranes, as well as in a variety of non-neuronal tissues including kidney. It is the product of the ANK2 gene (Otto et al., J. Cell Biol. 114: 241–53 (1991)). At least two alternatively spliced mRNA transcripts of 9 Kb and 13 Kb are generated from this gene (Kunimoto et al., J. Cell Biol. 115: 1319–31 (1991); Otto, J. Cell Biol. 114: 241–53 (1991)).

$Ank_G$ is an immunologically distinct isoform found at the plasma membrane at the nodes of Ranvier and at the axon initial segments (Kordeli et al., J. Cell Biol. 110: 1341–52 (1990); Kordeli and Bennett, J. Cell Biol. 114: 1243–59 (1991); Kordeli et al., J. Biol. Chem. 270: 2352–9 (1995)). It is the product of the ANK3 gene (Peters et al., J. Cell Biol. 130: 313–30 (1995)). Although two transcripts of the $Ank_G$ gene (15 Kb and 10 Kb) are neural-specific, smaller alternatively spliced isoforms may be expressed in kidney and lung (Kordeli et al., J. Biol. Chem. 270: 2352–9 (1995); Peters et al., J. Cell Biol. 130: 313–30 (1995)). In addition, a truncated ankyrin of 72 kilo-Daltons (kDa), which binds spectrin and is localized with the membrane protein GP85, has been detected immunologically in T-lymphocytes; its gene of origin is unknown (Bourguignon et al., *J. Cell Biol.* 102: 1463–73 (1986)).

Such isoform diversity may be critical to maintain a specific pattern of protein distribution in neurons and polarized epithelial cells such as those of the kidney tubules that directionally transport ions and nutrients. It is likely that such tissues harbor additional isoforms of ankyrin. Antibodies raised against $Ank_R$ recognize a 210 kDa product in erythrocytes, and a 190 kDa polypeptide in kidney tissue (Davis et al., 1989; Morrow et al., 1991). The $Ank_R$ from both sources binds spectrin and Na, K-ATPase (Devarajan et al., 1994). However, $Ank_R$-deficient NB/NB mice express the 190 kDa renal ankyrin, indicating that it is encoded by a gene distinct from ANK1, presumably an ANK3 gene (Bennett, 1992; Peters et al., 1993). Antibodies to $Ank_B$ cross-react with a 220 kDa peptide in kidney tissue, but $Ank_B$ cDNA probes hybridize only weakly to renal RNA (Otto et al., 1991), suggesting that the kidney $Ank_B$ peptide may also be the product of a distinct gene. Finally, antibodies to $Ank_G$ recognize polypeptides in the 190–72 kDa range in rat kidney (Kordeli et al., 1995), none of which have been further characterized.

After this work was first submitted, a report describing sequences $Ank_G$ in brain appeared (Kordeli et al., 1995). Comparing $Ank_{G119}$ with the $Ank_G$ observed in brain reveals the ankyrin cloned to be an alternative transcript of the larger form identified in brain. We therefore now term this form $Ank_{G119}$, rather than $Ank_K$ as previously reported in abstract form (Devarajan et al., 1995).

$Ank_{G119}$ possesses only part of the repeats domain characteristic of all previously described ankyrins, and also deletes almost the entire regulatory domain. $Ank_{G119}$ is expressed in kidney, placenta, and skeletal muscle, in Madin-Darby Canine Kidney (MDCK) cells (a collecting tubule line) and in cultured porcine proximal tubule cells (LLC-PK1). It is also present in low abundance in other cell types. The distribution of this small ankyrin in rat kidney cells and in confluent MDCK and LLC-PK1 cells is cytoplasmic and Golgi associated, unlike the plasma membrane localization of all other previously described ankyrin isoforms. $Ank_{G119}$ also specifically binds MDCK cell $\beta I\Sigma^*$ spectrin (erythroid like) in vitro with nanomolar affinity, and is coincidentally distributed in the Golgi apparatus with a previously described Golgi associated $\beta I\Sigma^*$ spectrin (Beck et al., 1994). These findings significantly extend the known diversity of the ankyrins, confirm the presence of a Golgi associated $\beta I\Sigma^*$ spectrin, and strongly imply that these two proteins function together as an integral part of the Golgi apparatus.

Cloning of $Ank_{G119}$

Figures 1C, 1D:
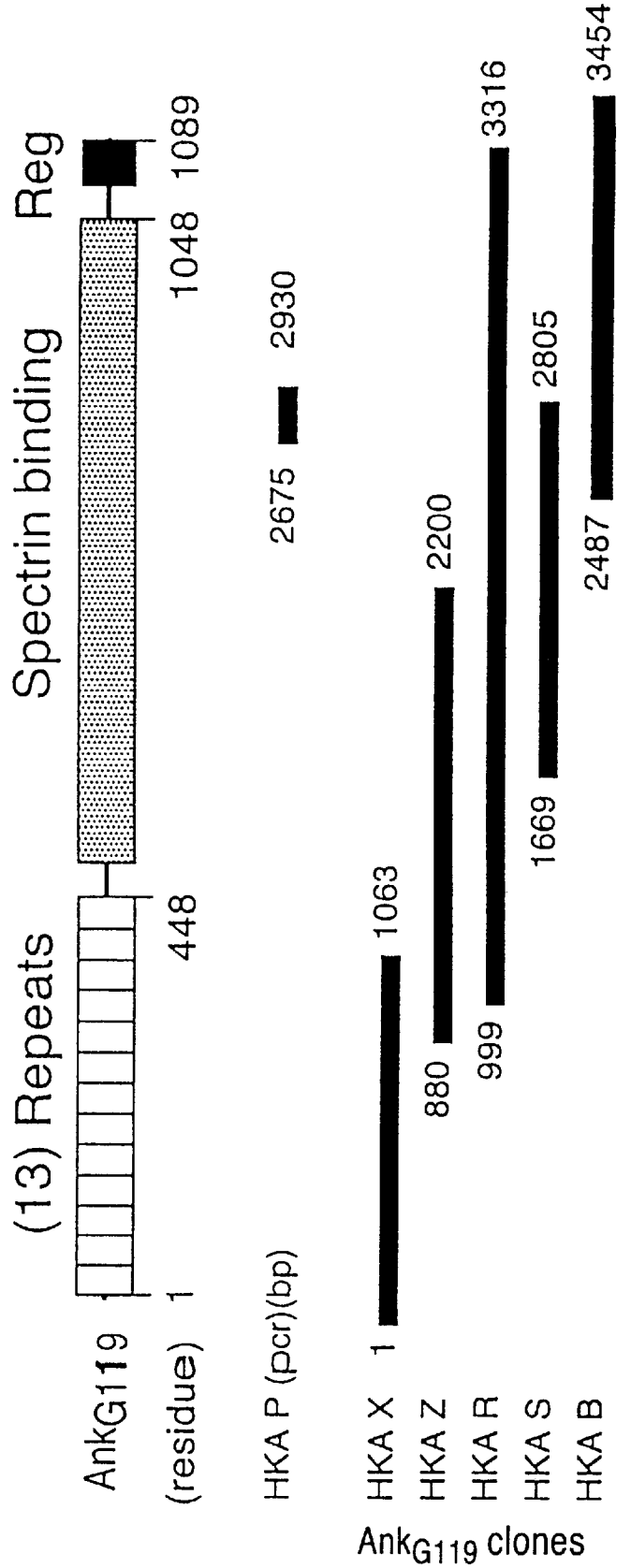
FIG. 1

FIG. 1(a). Primers flanking a 255 base pair (bp) conserved region in the spectrin-binding domains of previously described ankyrins were used to amplify a human kidney cDNA library (lane 2), rat kidney cDNA library (lane 3), reverse-transcribed rat kidney RNA (lane 4), reverse-transcribed MDCK cell RNA (lane 5), reverse-transcribed LLC-PK1 cell RNA (lane 6), and water (lane 7, negative control). Lane 1 contains a Hae III digest of fraction 174 (fx 174) as a standard. The 255 bp PCR product is indicated by the arrow. Ethidium bromide was used to stain the gel.

FIG. 1(b). The derived amino acid sequences of the clones generated from the PCR amplified cDNA from each sample fell into two related categories. Top, those related to $Ank_B$; bottom, those related to each other but distinct from $Ank_B$, comprising the new type of ankyrin called $Ank_{G119}$. The origin of the numbered sequences correspond to the numbered lanes in FIG. 1(a). CON depicts the consensus sequence. The sequence numbered 2 in the top grouping (the $Ank_B$ family) corresponds to lane 2 in FIG. 1(a) and is SEQ ID NO: 3. Similarly, the sequence corresponding to lane 3 is SEQ ID NO: 4; lane 4 is SEQ ID NO: 5; lane 5 is SEQ ID NO: 6; and lane 6 is SEQ ID NO: 7. The consensus sequence in the top grouping (labeled "Con") is SEQ ID NO: 8. The sequence numbered 2 in the bottom grouping (the $Ank_{G119}$ family) corresponds to lane 2 in FIG. 1(a) and is SEQ ID NO: 9. Similarly, the sequence corresponding to lane 3 is SEQ ID NO: 10; lane 4 is SEQ ID NO: 11; lane 5 is SEQ ID NO: 12; and lane 6 is SEQ ID NO: 13. The consensus sequence in the bottom grouping is SEQ ID NO: 14.

FIG. 1(c). Comparison of the derived human amino acid sequences of $Ank_R$ (SEQ ID NO: 15), $Ank_B$ (SEQ ID NO: 16, and $Ank_{G119}$ (SEQ ID NO: 17), over the amplified spectrin binding domain. Conserved amino acids are indicated by dashes. Human $Ank_B$ and $Ank_{G119}$ share 66% and 56% amino acid identity respectively to human $Ank_R$ over this region.

FIG. 1(d). Overlapping $Ank_{G119}$ clones obtained by screening a human kidney cDNA library first with the $Ank_{G119}$ PCR product (HKA B, S, R) and then with HKA R (HKA Z, X). Comparison of the full-length deduced amino acid sequence with $Ank_R$ and $Ank_B$ allowed the delineation of a 47 kDa domain consisting of 13 ankyrin repeats, a 67 kDa spectrin binding domain, and a very truncated 5 kDa regulatory domain.

FIG. 2

Nucleotide Sequence, Deduced Amino Acid Sequence and Putative Domain Structure of Human Kidney $Ank_{G119}$ The nucleotide sequence (also shown in SEQ ID NO: 1) and the amino acid sequence (also shown as SEQ ID NO: 2) is provided for human kidney $Ank_{G119}$. The beginning of each repeat is marked. The stop codons in all three reading frames upstream of the initiator methionine are underlined. The putative polyadenylation site is in bold and underlined. (GenBank #U43965, submitted Dec. 20, 1995; released Sep. 17, 1996).

FIG. 3

$ANK_{G119}$ Expression is Highest in a Restricted Subset of Human Tissues

A northern blot containing polyadenylate-selected mRNAs from human tissues was hybridized to a human $Ank_{G119}$ probe. Transcript size in kilobases (Kb) is indicated on the left; tissue source is as indicated. Note the presence of a prominent 6.0 Kb band in kidney, placenta, and skeletal muscle. The larger bands observed in brain and some other tissues reflect cross hybridization with other transcripts of $Ank_G$ (Kordeli et al., 1995). Hybridization of this blot with a human g actin probe revealed equal loading of all lanes (not shown).

FIG. 4

Figure 4A:
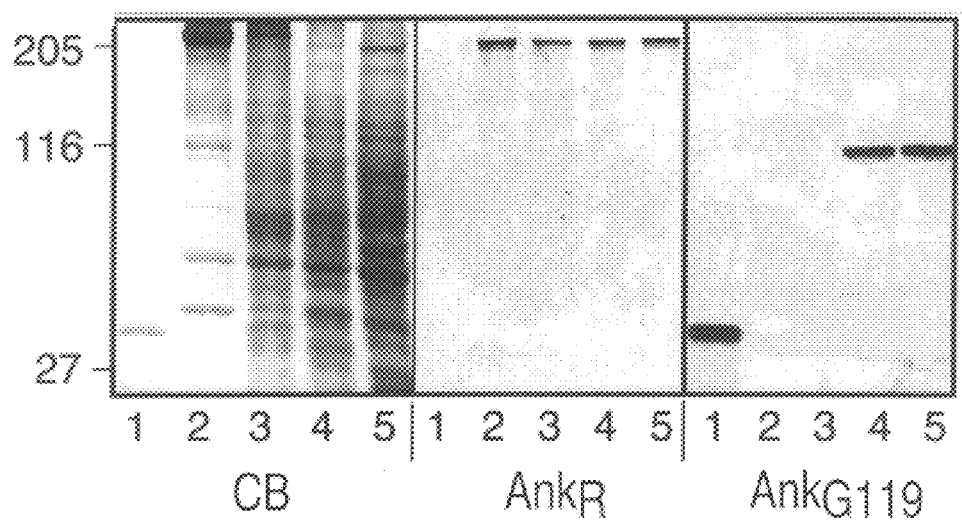

Antibodies to $Ank_{119}$ Identify a 116 kDa Protein in Kidney and Muscle Lysates FIG. 4(a). Polyclonal antibodies raised to a 37 kDa recombinant human GST-$Ank_{G119}$ fusion peptide or antibodies raised to $Ank_R$ were used to identify immunoreactive bands in various tissues. Lane 1, GST-$Ank_{G119}$ peptide alone; Lane 2, human erythrocyte ghosts; Lane 3, bovine brain (cortex); Lane 4, MDCK cells; Lane 5, mouse C2C12 (muscle) cells. Left panel, Coomassie blue stain; center panel, anti-$Ank_R$ Western blot; right panel, anti-$Ank_{G119}$ Western blot.

Figure 4B:
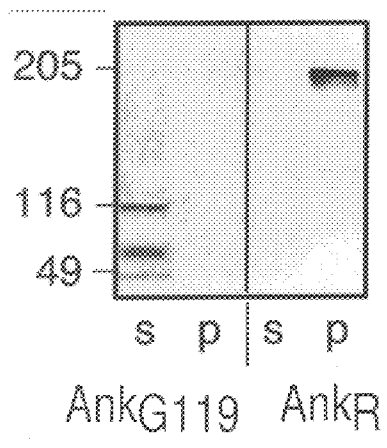

FIG. 4(b). Distribution of $Ank_{G119}$ and $Ank_R$ in rat renal cortical lysates. The Triton soluble (s) and insoluble pellet (p) fractions of rat renal cortical lysates were analyzed for the presence of $Ank_{G119}$ (left panel) or $Ank_R$ (right panel) by Western blot. Note that $Ank_{G119}$ distributed to the soluble fraction, while $Ank_R$ reacted with an approximately 190 kDa peptide in the pellet fraction.

Figure 4C:
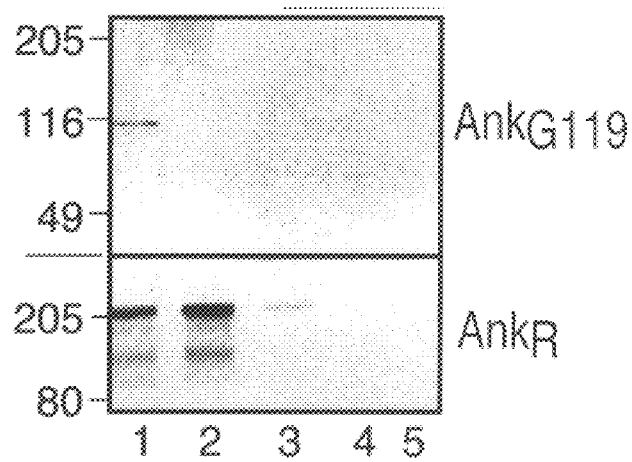

FIG. 4(c). Distribution of $Ank_{G119}$ and $Ank_R$ in MDCK cell lysates. Western analysis as above was carried out on sequentially extracted MDCK cell lysates (see methods). The fraction (fx) numbers are given. Note that all immunoreactive $Ank_{G119}$ was in the soluble fraction (fx1, lane 1) (top panel), while $Ank_R$ (~215 kDa in these canine cells) was predominately in the cytoskeletal fraction (fx2, lane 2), as previously noted (Devarajan et al., 1994).

FIG. 5

The Distribution of $Ank_{G119}$ is Cytoplasmic and Distinct From That of $Ank_R$ by Indirect Immunofluorescent Microscopy Cultured MDCK cells were fixed and immunostained after several days at confluence to determine the distribution of: (a, d), α-Na,K-ATPase; (b, e), $Ank_R$; and (c, f), $Ank_{G119}$. Note the punctuate cytoplasmic distribution of $Ank_{G119}$, compared to the plasma membrane compartmentalization of both $Ank_R$ and Na,K-ATPase. In such confluent and stably polarized cells, the association of $Ank_{G119}$ with Golgi membranes is largely inapparent (compare with FIG. 6). The Z-axis micrographs in (d, e, f) were constructed from a series of Z-axis line scans recorded at 1.2-μM levels, using the standard software of the BioRad 600 confocal microscope. Bar=10 μM.

FIG. 6

In Subconfluent MDCK cells, $Ank_{G119}$ and βIΣ* Spectrin Codistributes with β-COP, a Golgi Marker Cultured MDCK cells were sparsely plated, fixed and immunostained prior to achieving confluence. The distribution of $Ank_{G119}$ (a, d), βIΣ* spectrin (b, h), or β-COP (e, g) were determined by indirect immunofluorescence. Each row represents double immunostained preparations. The rightmost column (c, f, i) represents the appearance of the preparation in each row when viewed through a filter that passes the emission of both CY-2 (green) and CY-3 (red). Areas of absolute coincidence are revealed as yellow. Note the strong coincident staining over the Golgi complex. As seen in fully confluent MDCK cells, there is no staining at the plasma membrane. Bar=50 μM.

FIG. 7

$Ank_{G119}$ and βIΣ* Spectrin are Closely Co-distributed in Subconfluent MDCK Cells MDCK cells sparsely plated were stained for either βIΣ* spectrin monoclonal antibody, (mAb VIIIC7) (a) or $Ank_{G119}$ (b) as in FIG. 6. Their overlapping distributions are depicted by the yellow signal in (c). Note that with few exceptions, the two proteins are highly coincident. Bar=10 μM.

FIG. 8

The Protease Digestion Pattern of $Ank_{G119}$ is Distinct From $Ank_R$

Erythrocyte ghosts (left panel), or MDCK cells extracts of fraction one (fx1) (right panel) or fx2 (center panel) were partially digested with either μ-calpain or trypsin. Lanes 1 and 3, starting material; Lane 2, trypsin digest; Lane 4, μ-calpain digest. Each digest was immunoblotted with either anti-$Ank_{G119}$ or anti-$Ank_R$ antibodies, as indicated. Note that a 116 kDa peptide immunoreactive with $Ank_{G119}$ antibodies is not generated by proteolysis from any extract, and that the protease digestion pattern of $Ank_{G119}$ is distinct from that of $Ank_R$.

FIG. 9

$Ank_{G119}$ Binds to MDCK Cell Spectrin in vitro

Figure 9A:
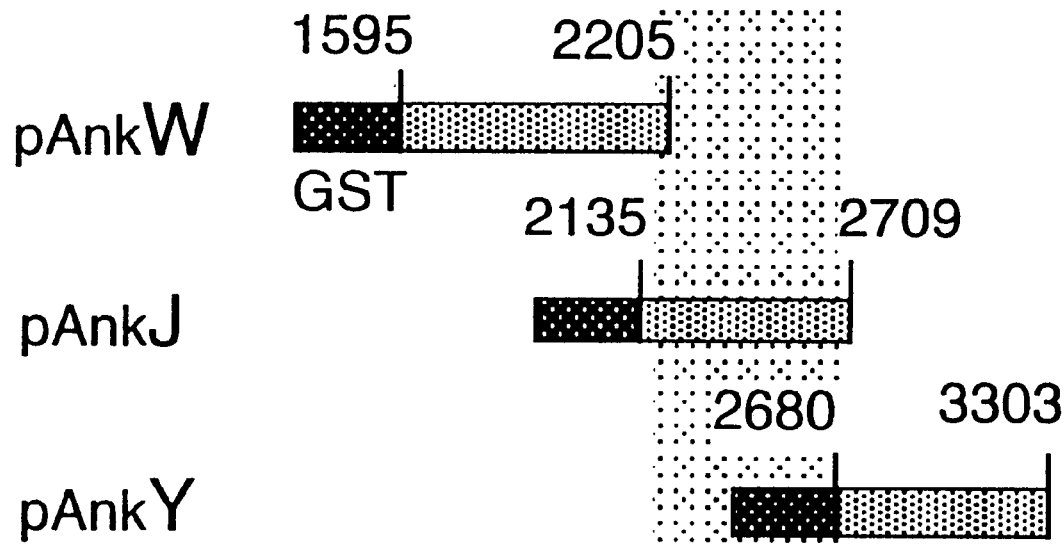
Figure 10:
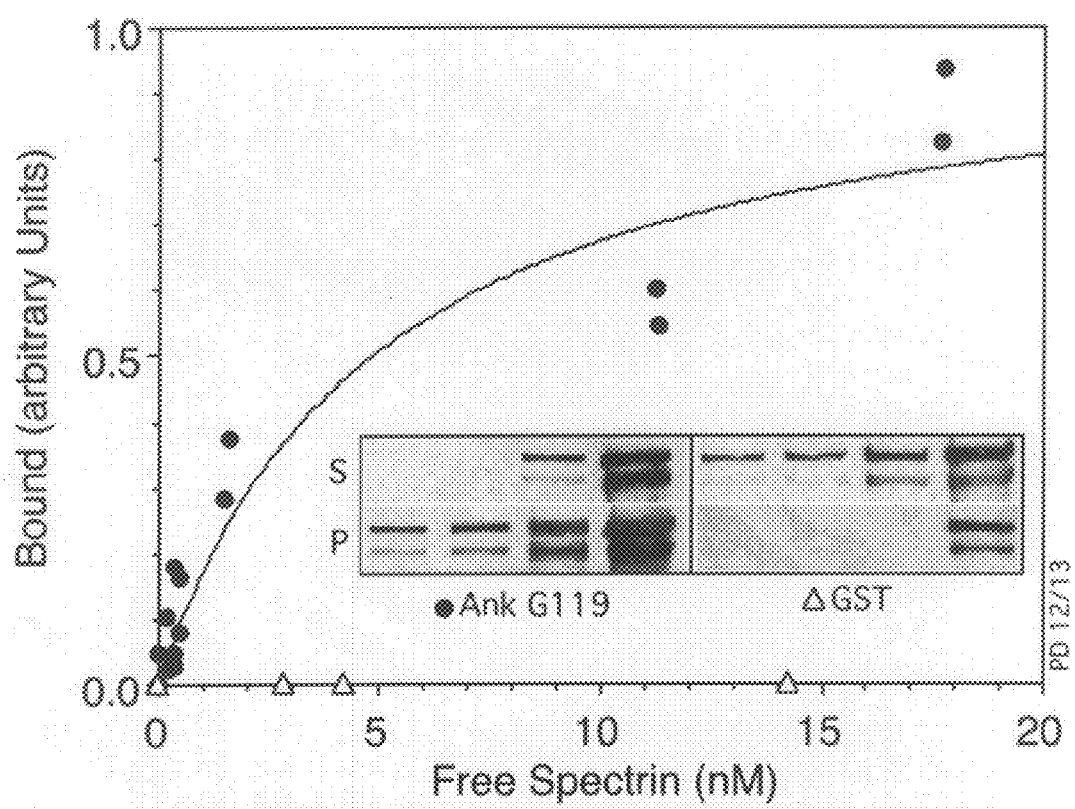

FIG. 9(a). The putative spectrin binding domain of $Ank_{G119}$ was expressed as three overlapping GST fusion peptides (pGEX2T-Ank W at 54 kDa; pGEX2T-Ank J at 48.5 kDa; pGEX1N-Ank Y at 50 kDa). The base pair (bp) positions of each construct with respect to the full-length clone is depicted. The relationship of these constructs to the full-length $Ank_{G119}$ amino-acid sequence is depicted in the bar at the top of the figure with the residue numbers indicated. The shaded area represents the minimal spectrin binding domain identified in these studies.

FIG. 9(b). (top) Coomassie blue stained SDS-PAGE gel showing respectively from left to right GST alone at 27.5 kDa, the Ank W, Ank J, and Ank Y fusion peptides, and the soluble fraction (fx1) from MDCK cell lysates. (bottom) Western blot of the lysate retained by each fusion peptide and of fx1 alone, using an antibody directed against βII spectrin. Note that only the Ank J construct interacted with βII spectrin in MDCK cell fx1.

FIG. 9(c). Western blot of the same lysate as in FIG. 9(b) that was retained by each fusion peptide and of fx1 alone, now using MAb VIIIC7 antibody directed against βIΣ* spectrin. Again, note that the Ank J peptide also interacts with this form of β spectrin from the MDCK cell fx1.

FIG. 10

$Ank_{G119}$ Binds βIΣ1 Spectrin Avidly

The interaction of $Ank_{G119}$ with biotinylated αIβ1 spectrin was measured quantitatively by incubating increasing amounts of biotinylated erythrocyte spectrin with a fixed amount of the pGEX2T-Ank J construct or GST alone, after which the Ank J peptide with any bound spectrin was separated by absorption to glutathione Sepharose, analyzed by SDS-PAGE, and the amount of bound spectrin determined (in arbitrary units) by overlay with HRP-avidin. The extent of binding is expressed as a fraction of the maximal binding (Bmax) estimated by non-linear regression analysis of the binding isotherm. The fitted curve yielded an estimated $K_d$=4.8±4.0 nM (±2 SD). (inset) Western blots of the supernatant (S) or pellet fractions (P) from one of the experiments demonstrating the specific binding of spectrin to the $Ank_{G119}$ construct.

SUMMARY OF THE INVENTION

The present invention provides novel proteins and nucleic acid sequences that encode $Ank_{G119}$ and its allelic variants. In a related embodiment, the invention provides a method of isolating novel ankyrin proteins, involving the probing of a target cDNA library or mRNA extract of a cell with an $Ank_{G119}$-encoding nucleic acid sequence or portions effective for use as a probe; and then isolating any cDNAs or mRNAs that hybridize under stringency conditions appropriate to detect their binding to said target.

In a further embodiment, the present invention relates to a host cell transformed with an $Ank_{G119}$-encoding nucleic acid sequence. Preferred hosts are prokaryotic hosts and eukaryotic hosts. The present invention also relates to a method for producing an $Ank_{119}$ protein comprising the step of culturing a host transformed with such a nucleic acid of claim under conditions in which the $Ank_{G119}$ protein is expressed. The invention further relates to isolated antibodies that bind to the $Ank_{G119}$ protein.

In yet a further embodiment, the present invention relates to a method for identifying agents that modulate the interaction of the $Ank_{G119}$ protein with ankyrin binding partners, comprising the steps of incubating the $Ank_{G119}$ protein or fragments and fusion proteins thereof with an agent to be tested, and then determining whether said agent modulates the binding of the $Ank_{G119}$ protein or fragments and fusion proteins thereof to the ankyrin binding partner. This method may be practiced with a cell extract. Various contemplated binding partners include proteins undergoing post-translational processing in the Golgi apparatus, such as integral membrane proteins or secretory proteins. A preferred ankyrin binding partner is spectrin.

The present invention also relates to a method for blocking the interaction of the $Ank_{G119}$ protein and its ankyrin binding partners, comprising the step of contacting a cell expressing the $Ank_{G119}$ protein with an agent selected by the foregoing methods to substantially block the interaction. Conversely, the invention relates to a method for enhancing the interaction of the $Ank_{G119}$ protein and its ankyrin binding partners, comprising the step of contacting a cell that expresses the $Ank_{G119}$ protein with an agent selected by the foregoing methods so as to enhance the interaction.

Also, the invention relates to methods of isolating ankyrin binding partners, comprising the steps of binding $Ank_{G119}$ polypeptides or fragments or fusion proteins thereof to a solid surface; contacting the bound $Ank_{G119}$ polypeptides or fragments or fusion proteins thereof with cell lysates; removing nonspecifically bound lysate components from the solid surface; and isolating the protein(s) that specifically bound to the $Ank_{G119}$ polypeptides or fragments or fusion proteins thereof.

DETAILED DESCRIPTION OF THE PREFERRED EMBODIMENT

I. General Description

This invention describes methods of identifying novel ankyrin forms. Identifying new ankyrins will be based on the isoform diversity that is characteristic to this protein. Different ankyrin subgroups, such as $Ank_R$, $Ank_B$ and $Ank_G$ are immunologically cross reactive. For example, antibodies raised against $Ank_R$ recognize a 210 kDa product in erythrocytes and a 190 kDa polypeptide in kidney tissue (Davis et al., 1989; Morrow et al., 1991). Additional novel forms of ankyrin can be detected using probes based on nucleotide domains that share a high degree of similarity within the ankyrin family. Another option would be to use nucleotide sequences that would be specific to one ankyrin subtype, such as $Ank_G$. One novel ankyrin, $Ank_{G119}$, has been isolated using such techniques.

II. Specific Embodiments

The specific embodiments disclosed in this invention relate to methods of identifying novel forms of ankyrin and their associated function in the Golgi apparatus, isolating the nucleic acids that encode the new ankyrins, characterizing these cDNA sequences and their associated protein products, identifying what tissues express these novel forms, ankyrin localization both in various tissues and intracellularly, developing methods to recombinantly express these novel ankyrin nucleic acid and protein sequences and protein ankyrins, and identifying the binding partners of said ankyrins.

A. Isolation of Other Ankyrin Encoding Nucleic Acid Molecules

Novel forms of ankyrin can be identified utilizing nucleotide sequences that possess observed regions of conservation. A comparison of published cDNA sequences encoding human erythrocyte (Lambert et al., 1990; Lux et al., 1990a) and brain (Otto et al., 1991) ankyrins reveal a conserved region in the spectrin-binding domain (between residues 1,183 and 1,268 of human erythrocyte ankyrin). Using this conserved region in conjunction with polymerase chain reaction (PCR) or reverse transcriptase PCR (RT-PCR) one can amplify additional ankyrin products from either cDNA libraries of both human and other species or messenger RNA (mRNA) from cells. Another embodiment uses nucleotide sequences in the region of nucleotide 669 to 860 of $Ank_{G119}$; this domain is 100% conserved with $Ank_G$, 80% with $Ank_B$ and 67% with $Ank_R$ (Devarajan et al., 1996).

Such a method was used to identify a conserved 255 base pair (bp) product from five kidney templates: a human kidney cDNA library, a rat kidney cDNA library, reverse-transcribed mRNA from MDCK cell extracts, reverse-transcribed mRNA from LLC-PK1 cell extracts, and reverse-transcribed mRNA from rat kidney cell extracts (FIG. 1a). Nucleotide sequencing of several positive clones from each of the PCR reactions detected two families of sequences. One family included proteins that were highly similar or identical to human brain ankyrin, reinforcing the immunologic data that $Ank_B$ is expressed in renal tissues (Otto et al., 1991). The other family of ankyrins ($Ank_G$) included sequences that were closely related to each other (>90% identity over the 255 bp region amplified by PCR), but dissimilar to any recognized ankyrins from brain or erythrocytes.

All molecular biological procedures were carried out using standard methods (Sambrook et al., 1989). Oligonucleotides bracketing the 255-bp conserved region within the spectrin-binding domain of human erythrocyte ankyrin were used in standard PCR reactions (Innis and Gelfand, 1990). The sense primer was 5'-GCCCAGTGGGAAGACATAACAGG-3' (SEQ ID NO:18), the antisense primer was 5'-CTTGTCCACTTATCATCTGTCATGCAG-3' (SEQ ID NO:19). Five templates were amplified: (a) human kidney cDNA library (Clontech Laboratories, Palo Alto, Calif.); (b) rat kidney cDNA library (Clontech); (c) rat kidney RNA reserve transcribed with random hexamer priming and avian myeloblastosis virus reserve transcriptase (Boehringer Mannheim Biochemicals, Indianapolis, Ind.); (d) MDCK cell RNA reverse transcribed as described above; and (e) LLC-PKI cell RNA reverse transcribed as described above. Water was used as a negative control for all PCR reactions. The absence of genomic DNA in the RNA samples was confirmed by the absence of amplified PCR products when no reserve transcriptase (RT) was used. The PCR products obtained were subcloned into the TA vector (Invitrogen, San Diego, Calif.), and both strands were sequenced by the dideoxynucleotide chain termination method (U.S. Biochemical Corp., Cleveland, Ohio). Subsequently, the random primer-labeled PCR product was used to screen the human kidney cDNA library to isolate several overlapping clones. One rescreening of the library was required to obtain the 5' end and complete the $ANK_{G119}$ cDNA sequence.

Once the sequence is obtained, the corresponding protein sequence can easily be deduced. Relevant binding domains and other important protein regions can be obtained when correlating the putative protein sequence with that of other known ankyrin protein sequences. This was performed for the nucleotide sequence of the human kidney $Ank_{G119}$ (FIG. 2). In the instance of $Ank_{G119}$, the number of repeats in the protein sequence are known. For the nucleotide sequence, the stop codons for all three reading frames and the putative polyadenylation site could also be readily identified (Devarajan et al., 1996).

B. Characterization of New Ankyrin Proteins

Several methods of characterizing the nucleotide and protein sequences of novel ankyrins exist, including computer modeling, recombinant techniques and immuno-methodologies. Identification and characterization of additional ankyrins can then be made using the information obtained from these approaches. The predominant method would use areas of sequence conservation, either at the protein or nucleotide levels, and more specifically within the spectrin-binding domains of the ankyrin proteins.

Initial characterization of the nucleotide and protein sequences can be performed by a number of molecular biology programs including TFASTA and BLAST for protein analysis and pairwise nucleotide sequence alignment using either Bestfit (Devereux et al., 1984) or MegAlign™ (DNASTAR, Inc.). For purposes of characterizing the function of certain domains within the novel ankyrin, embodiments would include developing recombinant methods of replicating the cDNA and expressing its associated protein product in cell expression systems, which are known to the skilled artisan. Such products could be used to develop antibodies or in binding assays as described in Devarajan et al., (1996).

Antibodies could be developed that recognize the conserved domains of the novel ankyrin to aid in binding assays. Alternatively, antibodies could be made which recognize sites unique to the novel ankyrin. For example, an antibody could be made that recognizes the carboxy terminus of $Ank_{G119}$, a region that appears unique to the $Ank_{G119}$ isoform (Devarajan et al., 1996). Antibodies would also be beneficial when performing binding assays such as those described by Devarajan et al., (1996), in competition assays used to ascertain the antibody's binding location and specificity, or to inhibit binding between ankyrin and other proteins it interacts with such as spectrin isoforms.

C. Methods to Identify Other Ankyrin Binding Partners

This invention also relates to methods of determining other proteins that bind to specific ankyrin isoforms. Identification of ankyrin binding partners is important in determining their role in the Golgi apparatus. Other binding partners include both spectrin and integral membrane proteins including those undergoing post-translational modification in the Golgi apparatus. One method of identifying ankyrin binding partners would be using antibodies or putative candidate ankyrin binding partners and performing immunofluorescence confocal microscopy or imnmunogold electron microscopy to determine whether proteins Codistributes within the cell together. If potential binding partners are found to co-distribute within the cell, then additional assays can be used to further investigate and characterize the binding of ankyrin to this other candidate protein.

The method of immunofluorescence confocal microscopy was used to examine the intracellular distribution of $Ank_{G119}$ and its distribution in comparison to other proteins found in the Golgi apparatus. In this manner, $Ank_{G119}$ was shown to co-distribute both with other Golgi markers, such as β-COP (Devarajan et al., 1996). β-COP is well characterized component of the cytoplasmic coatomer proteins that assemble on COP I vesicles involved in the transport of newly synthesized proteins between the ER, the Golgi, and the trans-Golgi network. (Pepperkok et al., 1993; Griffiths et al., 1995). It therefore makes a good positive control to show Golgi localization of new ankyrins. This method was also used when $Ank_{G119}$ was found to co-localize with βIΣ* spectrin, as revealed by its coincident immunostaining with mAb VIIIC7 (FIG. 6, *b* and *h*, and FIG. 7*b*).

To look at $Ank_{G119}$ its co-localization with other proteins at the intracellular level cells first were fixed and labeled in a modification of a previously used protocol for intact tissues (Van Why et al., 1992). Briefly, cells grown to confluence in Lab-Tek eight chamber slides were fixed by exchanging the tissue culture media with one rapid wash of PBS followed by Paraformaldehyde-Lysine-Periodate fixative (PLP) for a minimum of one hour at room temperature (McLean and Nakane, 1974). Cells were then washed thrice in PBS and used immediately for labeling or stored in holding buffer, (PBS 0.2% formaldehyde), at 4° C. for a maximum period of 10 days until labeling. On the day of labeling cells were gently permeabilized by freeze-thawing. In this procedure, cells were treated with PBS, 10% DMSO for 15 minutes, then rapidly frozen on an aluminum block at minus 35° C. They were then thawed by immersion in PBS, 1% BSA, 1% normal goat serum and allowed to remain in this solution in order to block non-specific staining for one hour at room temperature. Labeling of ankyrin antibodies was accomplished by exposing the cells to a titrated solution of pre-immune and immune sera diluted in PBS, 1% BSA, 0.1% normal goat serum for one hour at room temperature. Slides were gently agitated at 15 minute intervals. The cells were then thrice washed in PBS and biotinylated anti-rabbit secondary antibody (Vector Laboratories) was applied at a 1:100 dilution in PBS/BSA solution as with the primary antibodies. This was followed by a identical third step of exposing the cells to FITC conjugated avidin (Vector Laboratories) diluted 1/100 in PBS/BSA. Cells in adjacent chambers were labeled with a monoclonal antibody specific for Na,K-ATPase using a two step indirect labeling process involving exposure to the primary antibody, which was then followed after washing with rhodamine conjugated goat anti-mouse antibody (Cappel/Organon-Teknika) diluted 1/200 in PBS/BSA. The slides were cover-slipped in Vectashield (Vector Labs. Inc.) to retard fading, and were edge sealed with Cytoseal 60 (Stephens Scientific, Inc.) mounting media.

Figure 7:
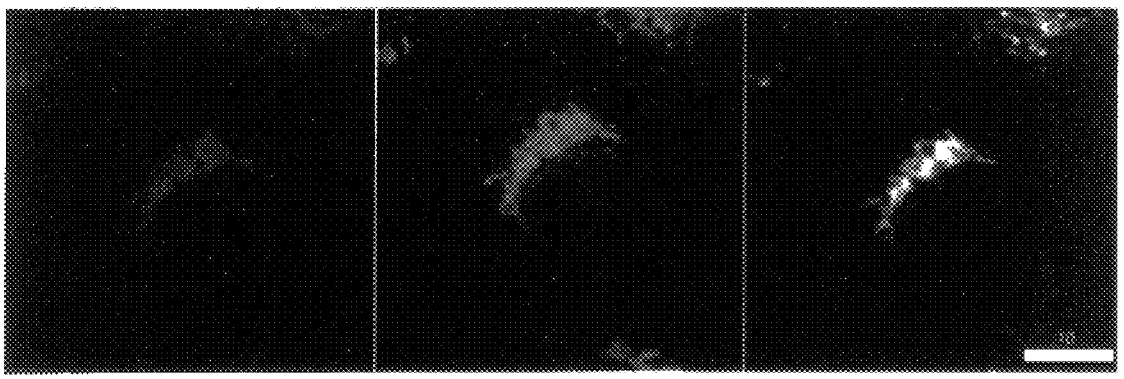

Confocal microscopy was performed using a Bio-Rad MRC-600 scanning laser microscope attached to a Zeiss Standard microscope with a Leitz 50X water immersion lens. Labeled cells and negative controls were first visualized en face under identical microscope settings which were standardized with respect to illumination intensity, detector amplifier settings, and confocal aperture size. Z section microscopy was also performed on areas of interest to determine apical and basolateral domain staining. In this procedure the confocal aperture was set at its minimum section thickness, ~1.0 micron with the objective lens used, and images were collected at ~1.2 micron steps in order that no overlap between sections would be observed. Alternatively, conventional indirect fluorescent microscopy was performed using an Olympus AX70 microscope equipped for epillumination. The results obtained using these methods is depicted in FIGS. 5, 6 and 7.

Other embodiments to ascertain ankyrin binding partners include competition assays and binding assays using the recombinant forms of the novel ankyrin or polypeptide sequences thereof. Another embodiment includes the use of fusion proteins where overlapping regions of the novel ankyrin are expressed and assayed for their abilities to retain a specific spectrin or other protein from cell lysates, as described by Devarajan et al., (1996) and described in detail below.

Immunoreactive assays, such as co-immunoprecipitations, could be used to ascertain whether a particular ankyrin binds a specific spectrin or other peripheral or integral membrane proteins. Another method to identify the spectrins or other proteins that bind ankyrin is surface plasmon resonance, which implements an apparatus called a BIACore (Pharmacia) to isolate new ligands. All these methods would aid in further characterizing the function of the novel ankyrin and the domains responsible for said function. Such methods are known to the skilled artisan.

D. Creating Antibodies to these Novel Ankyrin Binding Domains to Identify the Binding Domain As the spectrin-binding domains are highly conserved between ankyrin species, monoclonal and polyclonal antibodies and peptide-specific antibodies to this region could be created using techniques commonly known in the art. Antibodies could also be created by cleaving ankyrin with various proteases and raising antibodies to these ankyrin polypeptide cleavage products; these antibodies could be either polyclonal or monoclonal.

Antibodies to $Ank_{G119}$ were made and described in Devarajan et al., 820 (1996) by creating a fusion protein using a 255 base pair (bp) region that shares a high degree of similarity across ankyrin species, expressing the protein, immunizing the desired animal with said antigen, and assaying the sera obtained by ELISA to determine the specificity of the polyclonal antibody obtained.

Antibodies have been developed to $Ank_{G119}$ (Devarajan et al. (1996). Antibodies to $Ank_{G119}$ were produced from a recombinant peptide. The 255-bp PCR product from human kidney cDNA library was ligated in-frame to the expression vector pGEX-1N via the EcoR1 site. The pGEX vectors (Pharmacia Fine Chemicals, Piscataway, N.J.) direct the bacterial synthesis of foreign proteins as a fusion peptide with glutathione S-transferase (GST)(Smith and Johnson, 1988). Overnight cultures of transformed *Escherichia coli* were induced with 1 mM isopropyl-β-D-thiogalactoside for 5 h at 37° C., pelleted, and resuspended in sonication buffer (containing 50 mM Tris-HCl, 50 mM NaCl, 1 mM EDTA, 1mM PMSF, 10 µg/ml leupeptin, 10 µg/ml aprotinin, 1 mM DTT, 1 mM benzamidine, pH 8). After overnight storage at −80° C., the suspension was thawed, brought to 1% (vol/vol) Triton X-100, and sonicated at 70 W for 15 s, repeated three times with a sonic power apparatus (Branson Ultrasonics Corp, Danbury Conn.).

The lysate was centrifuged at 48,000 g for 20 min. and the supernatant was affinity purified on a 2-ml glutathione-agarose column. The pelleted material was extracted by solubilization in 6 M urea, 50 mM glycine, pH 9.0 and successively dialyzed in 2, 1, 0.5, and 50 mM urea (each with 50 mM glycine, pH 9.0) and then affinity purified as described before. Extraction of the pellet yielded a 25-fold increase in the amount of fusion peptide obtained. The two fractions were pooled, rebound to a glutathione-agarose column, eluted with 50 mM Tris-HCl/5 mM reduced glutathione, pH 8.0, and dialyzed into phosphate buffered sale (PBS). Aliquots were analyzed by SDS-PAGE, and 0.1 ml (at 40 mg/ml) was injected subcutaneously into New Zealand white rabbits in complete Freund's adjuvant for antibody production (Morrow et al., 1989). Antibody titers of hyperimmune sera were monitored by ELISA assay using recombinant $Ank_{G119}$.

E. Creating Polypeptides that Interfere with the Binding Domains of these Novel Ankyrins Recombinant forms of ankyrin or ankyrin specific polypeptide sequences can be created for use in binding and competition assays. Synthetic ankyrin peptides can also be produced using synthetic peptide synthesizers for the same purpose. Recombinant forms of ankyrin can be made by expressing the ankyrin gene or portions of the gene in-frame in a vector. Polypeptide sequences frequently can be expressed in the form of a fusion protein. These fusion proteins can be expressed in, amongst other things, bacteria such as *E. coli*.

Once prepared, such ankyrin polypeptide sequences can be utilized to characterize the binding domains of ankyrin specific antibodies and in binding assays to determine the binding sites of such binding partners as spectrin. $Ank_{G119}$ polypeptides were used to retain spectrin from whole cell lysates (Devarajan et al., 1994). These same polypeptides can also be implemented to measure quantitatively spectrin-ankyrin binding.

The interaction of $Ank_{G119}$ with βI spectrin was measured quantitatively using spectrin purified from fresh human erythrocytes (Morrow and Marchesi, 1981) and biotinylated by reaction of a 3 mg/ml solution in PBS with a 12 fold molar excess of Sulfo-NHS-Biotin (Pierce) at 0° C. for 2 hr. Excess biotin was removed by exhaustive dialysis against PBS. Recombinant $Ank_{G119}$ peptide or control GST was incubated overnight in PBS with increasing amounts of labeled spectrin. Bound and free fractions were separated by absorption to glutathione agarose as before (Kennedy et al., 1994), and analyzed by SDS-PAGE. Free and bound spectrin was measured by overlay assay using HRP-avidin and enhanced chemiluminescence (Kennedy et al., 1994). Each determination was compared to a series of standard protein loads employing the same biotinylated spectrin and developed on the same transfer membrane. Binding results were analyzed by nonlinear regression after subtraction of the non-specific binding to GST controls. All data was fitted as simple bimolecular binding, minimizing the degrees of freedom of the fit (Devarajan et al., 1996).

Once the nucleic acid sequence and its corresponding amino acid sequence are known for a new ankyrin, given the high degree of similarity between the forms of ankyrin in their spectrin-binding domains, these sequences may be useful in isolating additional ankyrins either through conserved or unique domains and hybridization, as was used to isolate the $Ank_{G119}$ gene described above.

F. Determining Intracellular Localization of these Novel Ankyrin Proteins

Intracellular localization of the novel ankyrin proteins can be performed using immunofluorescence and confocal microscopy or immunoperoxidase or immunogold and electron microscopy. In addition to determining whether the ankyrin protein under study localizes to the Golgi apparatus or specific portions of the Golgi apparatus, immunofluorescence microscopy can also observe whether a specific spectrin co-distributes with the ankyrin, which may infer that the spectrin is a binding partner to said ankyrin. For example, $Ank_{G119}$ was observed to colocalize with βIΣ* spectrin and was later identified as a binding partner of $Ank_{G119}$ (Devarajan et al., 1996). The methods used to demonstrate the intracellular localization of $Ank_{G119}$ has been described previously. Use of immunogold staining and electron microscopy techniques would be somewhat similar and such techniques are known to individuals skilled in the relevant art.

G. Determine Tissue Localization of these Novel Ankyrin Proteins

Once the new ankyrin gene is isolated, probes can be synthesized either using polymerase chain reaction (PCR) techniques or through in vitro transcription, of which both techniques are known to skilled artisans. These probes, which are typically radiolabeled, can be used to determine which tissues express a particular ankyrin gene via Northern blot analysis of RNA samples extracted from cells. The nucleic acid sequences used can be either highly conserved to several ankyrins or unique to the ankyrin of interest. For example, a unique 3' sequence of the $Ank_{G119}$ gene, which is observed in kidney tissue, could not amplify products from the brain (Devarajan et al., 1996).

Alternatively, one can use sequences that share a great degree of similarity across ankyrin subgroups. This would allow an individual skilled in the art to amplify products in tissues that correspond to the similar domains just be varying the stringency of the conditions used thereby assessing the tissue expression of an ankyrin. This method was used to observe $Ank_{G119}$ expression in the various tissues. A 255 bp probe specific to the spectrin-binding domain of several ankyrins was utilized to $Ank_{G119}$ mRNA expression. Human multiple-tissue nylon membrane blots containing poly-A selected mRNAs (Clontech) were hybridized to a random primer [$^{32}$P]-labeled cDNA probe (the 255 bp PCR product) encoding human kidney ankyrin or a control probe for actin and washed at high stringency. Hybridized bands were detected by autoradiography using Kodak X-OMAT film and fluorescent intensifying screens.

H. rDNA Molecules Containing a $Ank_{G119}$ Encoding Nucleic Acid Molecule

The present invention also claims methods for identifying additional novel ankyrins using $Ank_{G119}$ nucleic acid sequences. $Ank_{G119}$ is a novel truncated spectrin-binding ankyrin observed in kidney and muscle tissue that is associated with the Golgi apparatus. This molecule has many unusual features including: (1) the $Ank_{G119}$ cDNA clone has strong sequence homology within the spectrin-binding domain to other known ankyrins; (2) the putative regulatory domain of other known ankyrins is markedly truncated in $Ank_{G119}$ and what sequence exists in this domain is unique and unrelated to any other known ankyrin; (3) a large part of the 33-residue ankyrin repeat structure characteristic of this family of proteins is absent; (4) $Ank_{G119}$ expression is largely restricted to or, at least, most abundant in the kidney, placenta, and skeletal muscle; (5) $Ank_{G119}$ binds spectrin with high affinity; (6) $Ank_{G119}$ does not associate with the plasma membrane; (7) $Ank_{G119}$ and $\beta I\Sigma^*$ spectrin are colocalized with $\beta$-COP in incompletely polarized (Subconfluent) MDCK cells; and (8) $Ank_{G119}$ is a substrate in vitro for trypsin but resists $\mu$-calpain digestion (Devarajan et al., 1996). Additionally, $Ank_{G119}$ possesses unique 5' and 3' sequences indicating that perhaps $Ank_{G119}$ is tissue-specific, alternatively spliced and a truncated isoform of $Ank_G$ (Devarajan et al., 1996). These features are useful in determining what sequences to express recombinantly.

As one example, the nucleic acid sequences unique to $Ank_{G119}$, especially the 5' and 3' sequences, can be used to delineate other previously unidentified ankyrin isoforms that may possess these regions. Alternatively, the nucleic acid sequences responsible for encoding the spectrin-binding domain of $Ank_{G119}$, which is highly conserved among several ankyrin subgroups, can be used to identify new ankyrins across ankyrin subgroups. Another method of identifying additional ankyrins employs the spectrin-binding domain of other ankyrin nucleic acid sequences, including Ank W (1595–2205 bp; amino acid residues 457–692), Ank J (2135–2709 bp; amino acid residues 2135–2709) and Ank Y (2680–3303 bp; amino acid residues 850–1058) which is highly conserved (Devarajan et al., 1996). The use of these sequences was utilized in the isolation of $Ank_{G119}$. Such recombinant techniques are commonly known to individuals skilled in the art.

I. Host Cells Containing an Exogenously Supplied $Ank_{G119}$ Encoding Nucleic Acid Molecule The present invention further provides host cells transformed with a nucleic acid molecule that encodes an ankyrin protein, preferably the $Ank_{G119}$ of the present invention. The host cell can be either prokaryotic or eukaryotic. Eukaryotic cells useful for expression of an $Ank_{G119}$ protein are not limited, so long as the cell line is compatible with cell culture methods and compatible with the propagation of the expression vector and expression of the $Ank_{G119}$ gene product. Preferred eukaryotic host cells include, but are not limited to, yeast, insect and mammal cells, preferably vertebrate cells such as those from a mouse, rat, monkey or human fibroblastic cell line. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines.

Any prokaryotic host can be used to express an $Ank_{G119}$-encoding rDNA molecule. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc. Natl. Acad. Sci. USA* 69:2110, 1972; and Maniatis et al., *Molecular Cloning, A Laboratory Mammal*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol.* 52:456, 1973; Wigler et al., *Proc. Natl. Acad. Sci. USA* 76:1373–76, 1979.

Successfully transformed cells, i.e., cells that contain a rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503, 1975, or Berent et al., *Biotech.* 3:208, 1985 or the proteins produced from the cell assayed via an immunological method.

J. Methods to Identify Agents that Modulate the Binding of Ankyrin to its Binding Partners Another embodiment of the present invention provides methods for identifying agents that modulate, i.e., enhance or reduce, the association of an $Ank_{G119}$ with its binding partners such as spectrin or plasma membrane or secretory proteins. Thus, the present invention also provides methods to modulate the processing of integral membrane and secretory proteins.

With respect to identifying agents that inhibit or block, specifically, an ankyrin is mixed with a putative binding partner or a cellular extract containing a putative binding partner in the presence and absence of an agent to be tested. After mixing under conditions that allow association of the $Ank_{G119}$ or peptide with its binding partner, the two mixtures are analyzed and compared to determine if the agent reduced or blocked the association of the $Ank_{G119}$ or other novel ankyrins with its binding partners. Agents that block or reduce the association of an $Ank_{G119}$ or other novel ankyrins with binding to its partners such as spectrin, plasma membrane or secretory proteins will be identified as decreasing the amount of association present in the sample containing the tested agent. Similarly, agents that enhance or increase the association of an $Ank_{G119}$ or other novel ankyrins with or binding to its partners such as spectrin, plasma membrane or secretory proteins will be identified as increasing the amount of association present in the sample containing the tested agent.

As used herein, an agent is said to reduce or block $Ank_{G119}$ or other novel ankyrin-ankyrin binding partner associations when the presence of the agent decreases the extent to which or prevents the ankyrin binding partner from becoming associated with $Ank_{G119}$ or other novel ankyrin. One class of agents will reduce or block the association by binding to the ankyrin binding partner, while another class of agents will reduce or block the association by binding to $Ank_{G119}$ or other novel ankyrins. Conversely, as used herein, an agent is said to enhance $Ank_{G119}$ or other novel ankyrin-ankyrin binding partner associations when the presence of the agent increases the extent to which the ankyrin binding partner becomes associated with $Ank_{G119}$ or other novel ankyrin.

The ankyrin binding partner used in the above assay can either be an isolated and fully characterized protein, such as spectrin $\beta I\Sigma^*$ and $Ank_{G119}$ association, or the agent can be a partially characterized protein that binds to an ankyrin binding partner that has been identified as being present in a cellular extract. It will be apparent to one of ordinary skill in the art that so long as the ankyrin binding partner has been characterized by an identifiable property, e.g., molecular weight, the present assay can be used.

Agents that are assayed in the above method can be randomly selected or rationally selected or designed. As used herein, an agent is said to be randomly selected when the agent is chosen randomly without considering the specific sequences involved in the association of the $Ank_{G119}$ or other novel ankyrin with its ankyrin binding partner. An example of randomly selected agents is the use of a chemical library or a peptide combinatorial library, or a growth broth of an organism.

As used herein, an agent is said to be rationally selected or designed when the agent is chosen on a non-random basis, which takes into account the sequence of the target site and/or its conformation in connection with the agent's action. Agents can be rationally selected or rationally designed by utilizing the peptide sequences that make up the contact sites of the $Ank_{G119}$ or other novel ankyrin binding partners. For example, a rationally selected peptide agent can be a peptide whose amino acid sequence is identical to the ankyrin binding partner contact site on $Ank_{G119}$ or other novel ankyrin or the contact site located on the ankyrin's binding partner. Such an agent will reduce or block the association of the $Ank_{G119}$ or other novel ankyrins with its ankyrin binding partners by binding to the ankyrin binding partner or to $Ank_{G119}$ or to other novel ankyrins respectively.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of the cytoplasmic domain of an $Ank_{G119}$ or other novel ankyrins or with ankyrin binding partners such as spectrin $\beta I\Sigma^*$. Antibody agents are obtained by immunization of suitable mammalian subjects with peptides containing antigenic portions of $Ank_{G119}$, intended to be targeted by the antibodies. Critical regions include the contact sites involved in the association of the $Ank_{G119}$ or other novel ankyrins with their binding partners.

Antibody agents are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at either the amino or carboxy terminus with a cysteine (Cys) residue or interspersed with Cys residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the $Ank_{G119}$ or other novel ankyrin or signaling complex itself. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of $F(ab')_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin, humanized antibodies, or human antibodies.

The antibodies thus produced are useful not only as modulators of the association of an $Ank_{G119}$ or other novel ankyrins with its binding partner, but are also useful in immunoassays for detecting $Ank_{G119}$ or other novel ankyrins and for the purification of $Ank_{G119}$ or other novel ankyrins and their associated binding partners.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art.

EXAMPLES

Example 1

Cloning and Characterization of a Novel Ankyrin from Kidney Tissues ($Ank_{G119}$)

A comparison of published cDNA sequences encoding human erythrocyte (Lambert et al., 1990; Lux et al., 1990a) and brain (Otto et al., 1991) ankyrins revealed a region of sequence conservation in the spectrin-binding domain between residues 1,183 and 1,268 of human erythrocyte ankyrin. Oligonucleotides bracketing this highly conserved region amplified a 255 base pair (bp) product by PCR from five kidney templates: a human kidney cDNA library, a rat kidney cDNA library, reverse-transcribed MDCK cell RNA, reverse-transcribed LLC-PK1 cell RNA, and reverse-transcribed rat kidney RNA (FIG. 1a).

Nucleotide sequencing of several positive clones from each of the PCR reactions revealed that regardless of the templates used, just two families of sequences were detected (FIG. 1b). One family included proteins that were highly homologous or identical to human brain ankyrin, reinforcing immunologic data that $Ank_B$ is expressed in renal tissues (Otto et al., 1991). The other family of ankyrins ($Ank_G$) included sequences that were closely related to each other (>90% identity over the 255 bp region amplified by PCR), but dissimilar to any recognized ankyrins from brain cells or erythrocytes. Comparing the human sequences over this region, $Ank_{G119}$ displayed 58% and 64% identity at the nucleotide level (55–69% identity at the amino acid level) to $Ank_R$ and $Ank_B$ respectively (FIG. 1c). Subsequent comparisons to $Ank_G$ reveal 100% identity at the amino acid and DNA level over this region confirming that $Ank_{G119}$ arises from the same gene as $Ank_G$ (ANK3).

Using the 255 bp PCR product as a probe, three overlapping clones encoding a unique ankyrin sequence (HKA B, HKA S and HKA R) were identified in the human kidney cDNA library (FIG. 1d). Rescreening the library with HKA R yielded two additional overlapping clones (HKA Z and HKA X), confirming a contiguous 3,454 bp cDNA sequence for $Ank_{G119}$ (GenBank #U43965) with a putative polyadenylation signal (AATAAA) 17 bp upstream of the poly(A)$^+$ tail (FIG. 2). The cDNA sequence has a single open reading frame (with stop codons in all three reading frames upstream of the initiator methionine) and encodes 1,089 amino acid long protein with a predicted molecular weight of 119,201 Daltons and isoelectric point of 8.2.

Comparison of the deduced $Ank_{G119}$ amino acid sequence with previously described ankyrins allows for the delineation of three putative ankyrin domains (FIG. 2). Following a unique 5'-flanking sequence, $Ank_{G119}$ encodes just thirteen 33-residue repetitive motifs characteristic of the ankyrins, in contrast to the 22–24 copies of this motif found in all previously described ankyrins. As a result, domain I of $Ank_{G119}$ is 47 kDa.

The $Ank_{G119}$ repeats are identical to repeats 12–24 of $Ank_G$ and homologous to repeats 11–22 in $Ank_R$ and $Ank_B$, indicating that $Ank_{G119}$ is devoid of the first 10–11 repeats found in other ankyrins. The $Ank_{G119}$ repeat domain is followed by a 67 kDa putative spectrin binding domain with strong homology to other ankyrins, and a remarkably shortened 5 kDa regulatory domain (starting with A-L-R as in $Ank_R$) (Lux et al., 1990a), but then followed by unique sequence. This divergent regulatory domain cannot be an artifact of concatamer formation during library construction, since it has been identified in two distinct clones (FIG. 1), and (RT-PCR) reverse transcriptase PCR amplification of mRNA derived from kidney tissue using primers flanking the junction between the homologous ankyrin-like sequence and the novel 3' domain generated the predicted product (data not shown). Interestingly, these primers did not amplify any products from brain RNA, suggesting that end of $Ank_{G119}$ unique to it. Overall, $Ank_{G119}$ is highly homologous to $Ank_G$, and partially homologous to $Ank_B$ and $Ank_R$, suggesting that $Ank_{G119}$ is a tissue-specific, alternatively spliced and truncated isoform of $Ank_G$ that possesses unique 5' and 3' ends.

While the similarities noted above clearly indicate that it arises from the same gene, $Ank_{G119}$ differs from brain $Ank_G$ in several respects. Pairwise sequence alignment of $Ank_{G119}$ versus brain $Ank_G$ using either Bestfit (Devereux et al., 1984) or MegAlign™ (DNASTAR, Inc.) reveals five specific regions of deleted or altered sequence. The first 6 residues of $Ank_{G119}$ are unique, as are the first 385 residues of brain $Ank_G$. Compared to $Ank_G$, $Ank_{G119}$ deletes: (i) 18 residues between positions 850 to 869 of $Ank_G$; (ii) 6 residues between positions 912 to 919 of $Ank_G$; and (iii) 9 residues between $Ank_g$ positions 1,441 to 1,451. In addition, following residue 1,477 of $Ank_G$, $Ank_{G119}$ displays a unique 27 residue (amino acids residues 1,063 to 1,089) carboxy terminus, in contrast to the 901 residue (amino acid residues 1477 to 4378) carboxy-terminal domain of $Ank_G$. This may be why the 3' end of $Ank_{G119}$ was unable to amplify brain ankyrin mRNA (Devarajan et al., 1996).

Example 2

Tissue Specific Localization of $Ank_{G119}$ Determined by Northern Blot Analysis Using northern blot analysis, it was determined that $Ank_{G119}$ mRNA is expressed primarily in kidney, placenta and skeletal muscle tissue. $Ank_{G119}$ mRNA expression was ascertained using the 255 bp PCR product as a probe. Human multiple-tissue nylon membrane blots containing poly-A selected mRNAs (Clontech) were hybridized to the 255 base pair (bp) cDNA probe, a [$^{32}$P]-labeled random primer encoding human kidney ankyrin or a control probe for actin and washed at high stringency. The 255 bp probe revealed a major 6.0 kilobase (Kb) transcript in human kidney, placenta, skeletal muscle, and rat kidney tissue.

Figure 3:
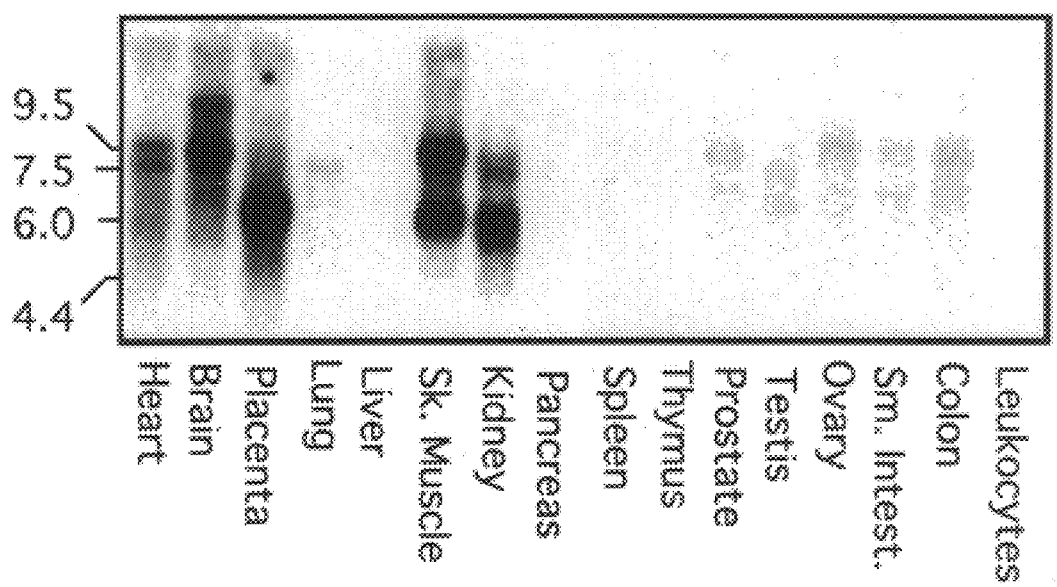

Upon longer exposures, the $Ank_{G119}$ cDNA probe also hybridized with a 7 Kb message in kidney tissue, 9 Kb and 14 Kb species in brain, 8 and 9 Kb messages in heart, and faint 7–8 Kb messages in intestinal tissues and ovary (FIG. 3). No message was detected in leukocytes or in liver cells.

Presumably, these weak bands represent either cross-hybridization with other ankyrins as a result of the strong sequence conservation between different ankyrins over some part of their structure, or more likely, other alternatively spliced products of the $Ank_G$ gene (Kordeli et al., 1995; Peters et al., 1995). Hybridization of these blots after stripping of the $Ank_{G119}$ cDNA probe with a human g actin cDNA probe revealed equal loading of actin message in all lanes.

Example 3

Tissue Specific Localization of $Ank_{G119}$ Using Antibodies

A recombinant peptide representing the 255 base pair (bp) PCR product of $Ank_{G119}$ (clone HKA P, FIG. 1) was prepared and purified as a fusion protein with glutathione-S-transferase (GST). This peptide was used to generate a polyclonal antibody that specifically recognised this fusion protein on Western blots (FIG. 4). This $Ank_{G119}$ specific antibody did not react with any proteins in erythrocyte ghosts or in bovine brain cells. A protein with an apparent molecular weight (MW) of 116 kDa was detected in MDCK cells and in C2C12 cells, a myoblast cell line. By comparison, an antibody to $Ank_R$ detected immunoreactive bands between 190–220 kDa in all cell samples, representing previously described ankyrin species. These observations were refined by examining the solubility properties of the peptide being detected by the anti-$Ank_{G119}$ antibody. Unlike the 190 kDa ankyrin recognized by $Ank_R$ specific antibodies, the 116 kDa $Ank_{G119}$ was present only in the Triton soluble fraction of rat kidney cortical tissue (FIG. 4b).

Example 4

Preparation of $Ank_{G119}$ Specific Polyclonal Antibodies

Antibodies to $Ank_{G119}$ were produced from a recombinant peptide. The 255 bp PCR product from the human kidney cDNA library was ligated in-frame to the expression vector pGEX-1N, via the Eco R1 site. The pGEX vectors (Pharmacia) direct the bacterial synthesis of foreign proteins as a fusion peptide with glutathione S-transferase (GST) (Smith and Johnson, 1988). Overnight cultures of transformed E. coli were induced with 1 mM isopropyl β-D-thiogalactoside for 5 hrs at 37° C., pelleted and resuspended in sonication buffer (containing 50 mM Tris-HCl, 50 mM NaCl; 1 mM EDTA, 1 mM phenylmethylsulfonyl fluoride (PMSF), leupeptin (10 mg/ml), aprotinin (10 mg/ml), 1 mM dithiothreitol (DTT), 1 mM benzamidine, pH 8). Following overnight storage at −80° C., the suspension was thawed, brought to 1% (v/v) Triton X-100, and sonicated at 70 W for 15 seconds, repeated three times, with a Branson® sonic power apparatus. The lysate was centrifuged at 48,000 x g for 20 minutes and the supernatant affinity-purified on a 2-ml glutathione-agarose column. The pelleted material was extracted by solubilization in 6 M urea, 50 mM glycine, pH 9.0, and successively dialyzed in 2 M, 1 M, 0.5 M, and 50 mM urea (each with 50 mM glycine, pH 9.0), and then affinity purified as before. Extraction of the pellet yielded a 25-fold increase in the amount of fusion peptide obtained. The two fractions were pooled, rebound to a glutathione-agarose column, eluted with 50 mM Tris-HCl, 5 mM reduced glutathione, pH 8.0, and dialyzed into phosphate buffered saline. Aliquots were analyzed by SDS-PAGE, and 0.1 ml (at 40 mg/ml) was injected subcutaneously into New Zealand white rabbits in complete Freund's adjuvant for antibody production (Morrow et al., 1989). Antibody titers of hyperimmune sera were monitored by ELISA assay using recombinant $Ank_{G119}$.

Example 5

$Ank_{G119}$ Codistributes with Golgi Markers and βIΣ* Spectrin

One method of determining the intracellular distribution of a particular ankyrin can be through the use of immunofluorescence confocal microscopy. This method can also ascertain distribution of possible spectrins that bind to a particular ankyrin. Immunofluorescence confocal microscopy with $Ank_{G119}$ antibodies produced a largely diffuse but punctuate cytoplasmic staining in stable and highly confluent MDCK cells (FIG. 4c and f), as well as in LLC-PK1 cells and in intact renal tubule cells (data not shown). In contrast, antibodies directed against $Ank_R$ demonstrated a basolateral and somewhat apical membrane distribution (FIG. 4b and e), while the distribution of the α subunit of Na,K-ATPase (FIG. 4a and d) was basolateral, as expected in these mature MDCK cells. The αIIβII spectrin (fodrin) in these cells was also predominantly localized to the basolateral membrane (data not shown) (Nelson and Veshnock, 1986; Koob et al., 1988; Morrow et al., 1989).

Figures 5A, 5B, 5C, 5D, 5E, 5F:
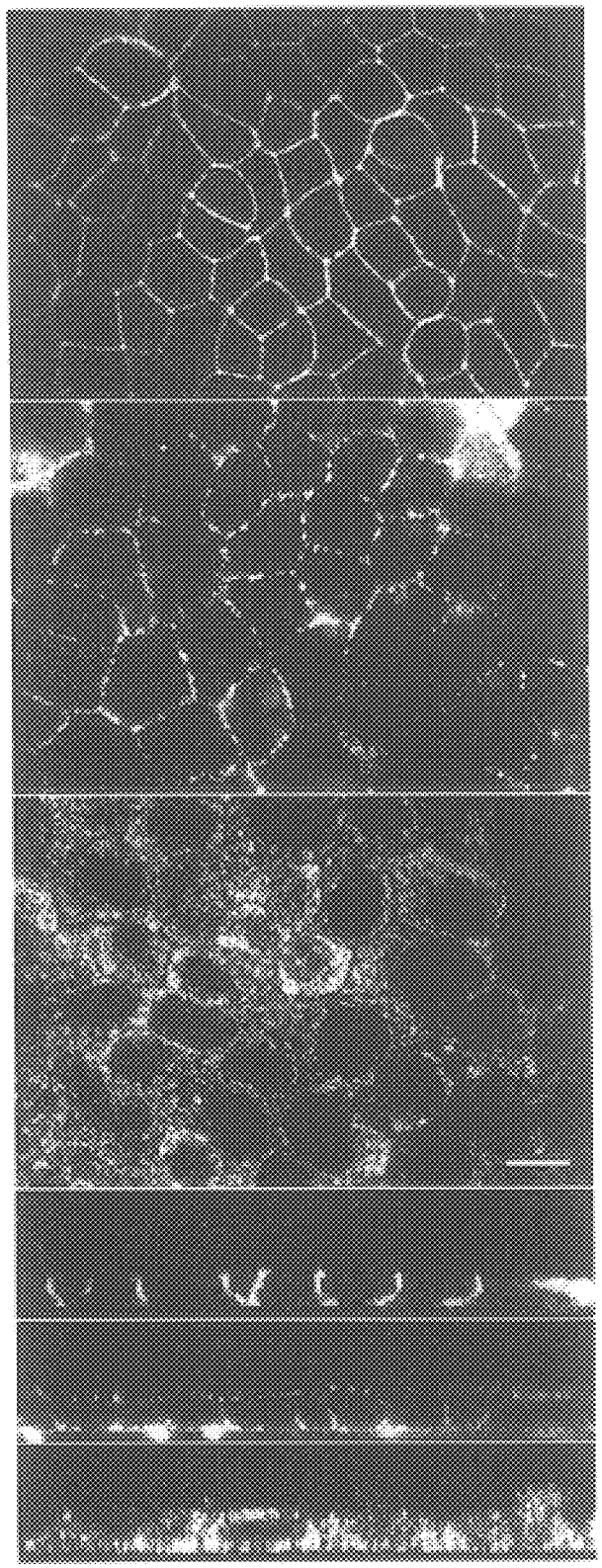
Figure 6A:
Figure 6B:
Figure 6C:
Figure 6D:
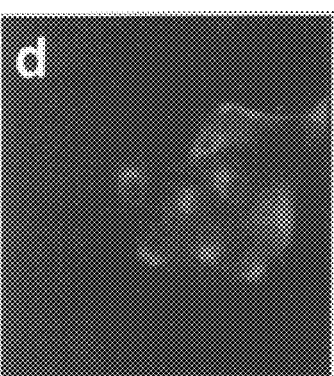
Figure 6E:
Figure 6F:
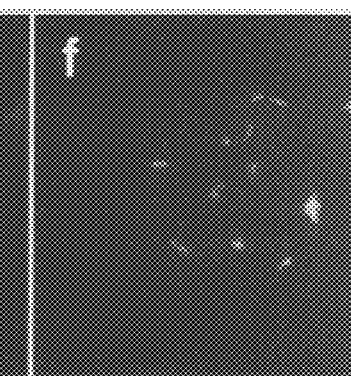
Figure 6G:
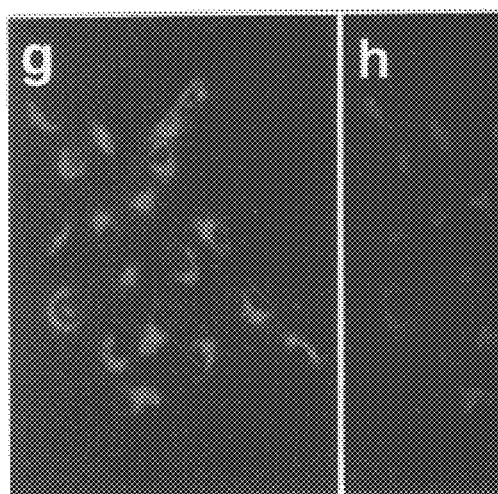
Figure 6H:
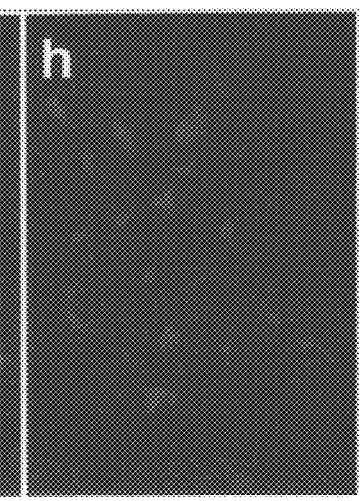
Figure 6I:
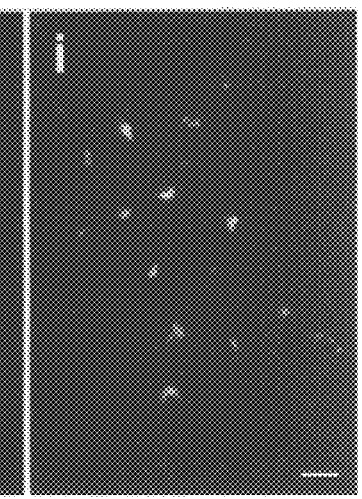

When isolated or Subconfluent MDCK cells were examined, a different intracellular distribution of $Ank_{G119}$ became apparent (FIGS. 5 and 6). Under these conditions, in which full epithelial cell polarity had not yet been established, intense anti-$Ank_{G119}$ staining was concentrated eccentrically near the nucleus, with less punctuate cytoplasmic staining apparent (FIG. 5a and d; FIG. 6a). This pattern was strongly suggestive of Golgi staining and was confirmed as such by its coincident staining pattern of β-COP (FIG. 5e and g). β-COP is the best characterized component of the cytoplasmic coatomer proteins that assemble on COP-I vesicles involved in the transport of newly synthesized proteins between the endoplasmic reticulum (ER), the Golgi, and the trans Golgi network (Pepperkok et al., 1993; Griffiths et al., 1995). Recent data has also implicated β-COP in the function of some types of endosomes (Whitney et al., 1995). Using immunofluorescence confocal microscopy, $Ank_{G119}$ was also found to be co-localized in the Golgi with βIΣ* spectrin, as revealed by its coincident immunostaining with MAb VIIIC7 (FIG. 5b and h; FIG. 6b).

Example 6

Identification of Specific Spectrin-Ankyrin Interactions

Figure 8:
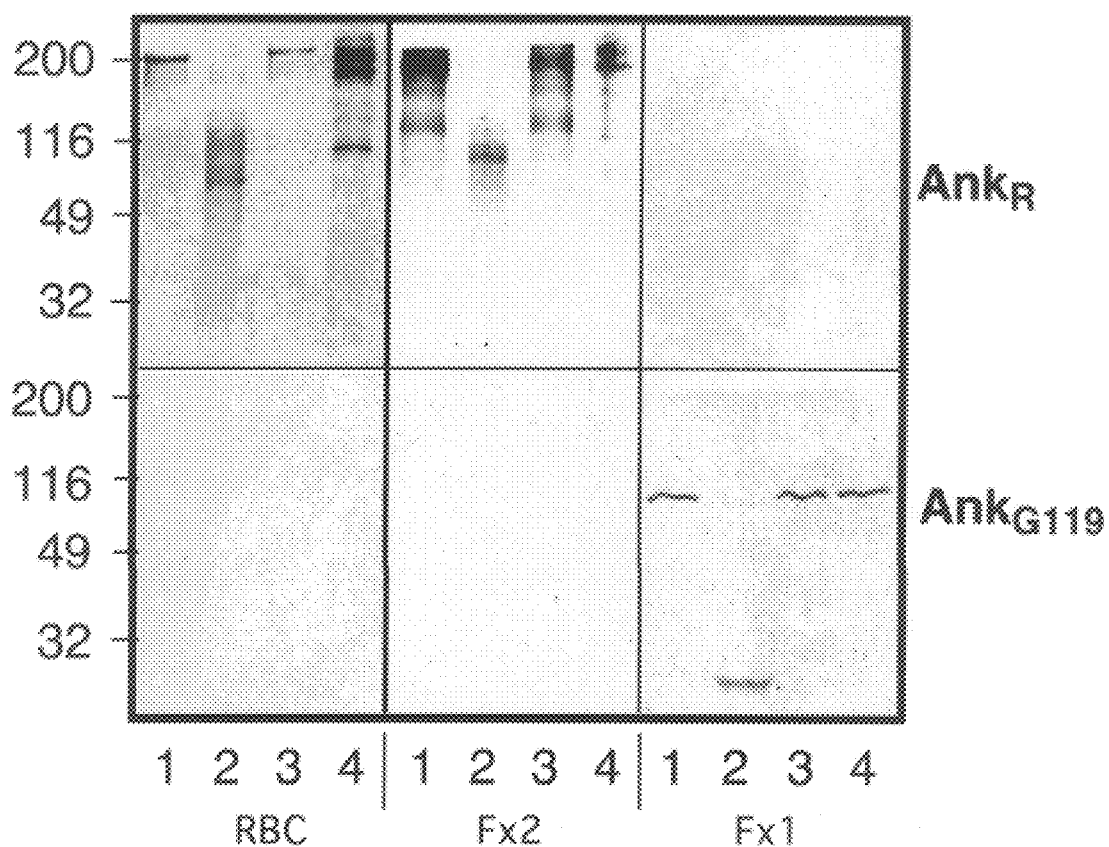

Since $Ank_{G119}$ was identified using the highly conserved spectrin-binding domain, it was of interest to determine whether the 116 kDa $Ank_{G119}$ retained spectrin binding activity. Fusion proteins expressing $Ank_{G119}$ sequences were assayed for their binding ability to the βI and βII forms of spectrin in vitro. The putative spectrin binding domain of $Ank_{G119}$ was expressed in bacteria as three overlapping GST fusion peptides (FIG. 8a) purified over a bioaffinity column and assayed for its ability to retain spectrin from the soluble fraction (fx1) of MDCK cell lysates. Each of the recombinant peptides was soluble, stable and of the molecular weight predicted by SDS-PAGE analysis (FIG. 8b). Only peptide pGEX-HKA J specifically and reproducibly bound both βII spectrin (FIG. 8b) and βI spectrin (FIG. 8c). This peptide represents amino acid residues 669–860 of $Ank_{G119}$ (shaded area in FIG. 8), a region highly conserved between all known ankyrin isoforms (100% homology with $Ank_G$; 80% with $Ank_B$; and 67% with $Ank_R$). Interestingly, the spectrin-binding domain previously identified in residues 1136–1160 of $Ank_R$ (Platt et al., 1993) is highly homologous to $Ank_{G119}$ residues 801–825 contained within the spectrin-binding recombinant peptide pGEX-HKA J.

Given the coincident localization of $Ank_{G119}$ with $\beta I\Sigma^*$ spectrin in MDCK cells (FIG. 7), the strength of the interaction between these proteins was of interest. The $\beta I\Sigma^*$ spectrin in kidney cells remains incompletely characterized, although immunologically it is most similar to the $\beta I\Sigma 1$ spectrin from erythrocytes (Beck et al., 1994), a point further confirmed by its reactivity with MAb VIIIC7 reported here. Therefore, the ability of the $Ank_{G119}$ spectrin-binding domain to associate with $\beta I\Sigma 1$ spectrin from red blood cells was measured (FIG. 9). These two proteins interacted strongly, with an apparent $K_d=4.2\pm4.0$ (2 SD) nM.

The interaction of $Ank_{G119}$ with $\beta I$ spectrin was measured quantitatively using spectrin purified from fresh human erythrocytes (Morrow and Marchesi, 1981) and biotinylated by reaction of a 3 mg/ml solution in phosphate buffered saline (PBS) with a 12 fold molar excess of Sulfo-NHS-Biotin (Pierce) at 0° C. for 2 hr. Excess biotin was removed by exhaustive dialysis against PBS. Recombinant $Ank_{G119}$ peptide or control GST was incubated overnight in PBS with increasing amounts of labeled spectrin. Bound and free fractions were separated by absorption to glutathione agarose as before (Kennedy et al., 1994) and analyzed by SDS-PAGE. Free and bound spectrin was measured by an overlay assay using HR-P-avidin and enhanced chemiluminescence (Kennedy et al., 1994). Each determination was compared to a series of standard protein loads employing the same biotinylated spectrin and developed on the same transfer membrane. Binding results were analyzed by non-linear regression after subtraction of the non-specific binding to GST controls. All data was fitted as simple bimolecular binding, minimizing the degrees of freedom of the fit.

Example 7

Characterization of Novel Ankyrins using Proteolytic Digestion

The 116 kDa $Ank_{G119}$ is not a proteolytic fragment of other identified ankyrins as demonstrated through proteolytic digestion. This method can be employed to characterize new forms of ankyrin. Previous work demonstrated that proteolysis of ankyrin from either brain or red blood cells yields fragments in the size range of 40 to 120 kDa, and that many of these fragments lacked the putative membrane binding domain (Davis and Bennett, 1984; Weaver et al., 1984). Therefore, the reactivity of the anti-$Ank_{G119}$ antibody with proteolytic fragments of conventional renal ankyrins was of concern.

To exclude the possibility that the anti-$Ank_{G119}$ was recognizing only a new epitope created by the proteolysis of a conventional ankyrin, extracts of MDCK cells were subjected to proteolysis using either $\mu$-calpain or with trypsin, and the resulting break-down products examined by Western blotting with either the $Ank_{G119}$ or $Ank_R$ antibodies. Erythrocyte ghosts were also examined in these assays.

Both the conventional 210 kDa renal ankyrin (recognized by anti-$Ank_R$ in the cytoskeletal fraction, fx2) and the 116 kDa $Ank_{G119}$ (in the soluble fraction, fx1) were degraded by these proteases (FIG. 7). The $Ank_{G119}$ antibody reacted with a breakdown product at ~20 kDa in the soluble fraction after trypsin treatment. No breakdown products were detected after $\mu$-calpain treatment. The $Ank_R$ antibody recognized an array of breakdown products after both $\mu$-calpain and trypsin treatment in both erythrocyte membranes and in the cytoskeletal fraction of MDCK cells, although the fragmentation patterns were not identical (FIG. 7). Importantly, at no point in the proteolysis of the cytoskeletal fraction of MDCK cells or of red cell ghosts was a 116 kDa peptide generated that would react with the $Ank_{G119}$ antibody. The pattern of fragments generated from the proteolysis of $Ank_{G119}$ was also not a subset of the fragments generated by similar conditions of proteolysis of the $Ank_R$ based on their molecular weights. These distinct patterns of proteolytic breakdown and immunoreactivity between renal $Ank_{G119}$ and $Ank_R$ indicate that the 116 kDa $Ank_{G119}$ immunoreactive protein observed in the cytoplasmic pool cannot be merely a proteolytic fragment of a conventional membrane-associated renal ankyrin.

It should be understood that the foregoing discussion and examples merely present a detailed description of certain preferred embodiments. It therefore should be apparent to those of ordinary skill in the art that various modifications and equivalents can be made without departing from the spirit and scope of the invention. All articles and other texts that are identified in this patent application or the following list of literature cited are incorporated by reference in their entirety.

Literature Cited

Axton, J. M., F. L. Shamanski, L. M. Young, D. S. Henderson, J. B. Boyd and W. T. Orr. 1994. The inhibitor of DNA replication encoded by the Drosophila gene plutonium is a small, ankyrin repeat protein. *Embo J* 13:462–70.

Beck, K. A., J. A. Buchanan, V. Malhotra and W. J. Nelson. 1994. Golgi spectrin: identification of an erythroid beta-spectrin homolog associated with the Golgi complex. *J. Cell Biol.* 127:707–23.

Bennett, V. 1992. Ankyrins. Adaptors between diverse plasma membrane proteins and the cytoplasm. *J Biol Chem* 267:8703–6.

Bennett, V. and D. M. Gilligan. 1993. The spectrin-based membrane skeleton and micron-scale organization of the plasma membrane. *Annu Rev Cell Biol* 9:27–66.

Bensadoun, A. and D. Weinstein. 1976. Assay of proteins in the presence of interfering materials. *Anal. Biochem.* 70:241–250.

Birkenmeier, C. S., R. A. White, L. L. Peters, E. J. Hall, S. E. Lux and J. E. Barker. 1993. Complex patterns of sequence variation and multiple 5' and 3' ends are found among transcripts of the erythroid ankyrin gene. *J Biol Chem* 268:9533–40.

Bork, P. 1993. Hundreds of ankyrin-like repeats in functionally diverse proteins: mobile modules that cross phyla horizontally? *Proteins* 17:363–74.

Bourguignon, L. Y., G. Walker, S. J. Suchard and K. Balazovich. 1986. A lymphoma plasma membrane-associated protein with ankyrin-like properties. *J Cell Biol* 102:2115–24.

Chan, W., E. Kordeli and V. Bennett. 1993. 440-kD ankyrinB: structure of the major developmentally regulated domain and selective localization in unmyelinated axons. *J Cell Biol* 123:1463–1473.

Chomczynski, P. and N. Sacchi. 1987. Single step method of RNA isolation by acid guanidinium thiocyanate-phenol-chloroform extraction. *Anal. Biochem.* 162:156–159.

Davis, J., L. Davis and V. Bennett. 1989. Diversity of membrane binding sites of ankyrins. *J. Biol. Chem* 264:6417–6426.

Davis, J. Q. and V. Bennett. 1984. Brain ankyrin. A membrane-associated protein with binding sites for spectrin, tubulin, and the cytoplasmic domain of the erythrocyte anion channel. *J Biol Chem* 259:13550–9.

Davis, J. Q. and V. Bennett. 1990. The anion exchanger and Na+K(+)-ATPase interact with distinct sites on ankyrin in in vitro assays. *J Biol Chem* 265:17252–6.

Davis, L. H., E. Otto and V. Bennett. 1991. Specific 33-residue repeat(s) of erythrocyte ankyrin associate with the anion exchanger. *J Biol Chem* 266:11163–9.

Devarajan, P., A. Mann, T. Ardito, P. Stabach, M. Kashgarian and J. S. Morrow. 1995. A truncated cytoplasmic isoform of ankyrin binds fodrin in kidney. *Molec.Biol.Cell* 6:269a.

Devarajan, P. and J. S. Morrow (1996a). The Spectrin Cytoskeleton and Organization of Polarized Epithelial Cell Membranes. *Membrane Protein-Cytoskeleton Complexes: Protein Interactions, Distributions and Functions.* W. J. Nelson, Ed. New York, Academic Press. (in press).

Devarajan, P., D. A. Scaramuzzino and J. S. Morrow. 1994. Ankyrin binds to two distinct cytoplasmic domains of Na,K-ATPase a subunit. *Proc. Natl. Acad. Sci. (USA)* 91:2965–2969.

Devarajan, P., Stabach, P. R. Mann, A. S., Ardito, T., Kashgarian, M., and J. S. Morrow. 1996b. Identification of a small cytoplasmic ankyrin (AnkG119) in kidney and muscle that binds βIΣ* spectrin and associates with the Golgi apparatus. *Journal Cell Biol,* 133:819–830.

Devereux, J., P. Haeberli and O. Smithies. 1984. A comprehensive set of sequence analysis programs for the VAX. *Nucleic Acids Res.* 12:387–395.

Diederich, R. J., K. Matsuno, H. Hing and T. S. Artavanis. 1994. Cytosolic interaction between deltex and Notch ankyrin repeats implicates deltex in the Notch signaling pathway. *Develop* 120:473–81.

Dubreuil, R. R. and J. Yu. 1994. Ankyrin and beta-spectrin accumulate independently of alpha-spectrin in Drosophila. *Proc. Natl. Acad. Sci. (USA)* 91:10285–9.

Gallagher, P. G., W. T. Tse, A. L. Scarpa, S. E. Lux and B. G. Forget. 1992. Large numbers of alternatively spliced isoforms of the regulatory region of human erythrocyte ankyrin. *Trans Assoc Am Physicians* 105:268–77.

Griffiths, G., R. Pepperkok, J. K. Locker and T. E. Kreis. 1995. Immunocytochemical localization of beta-COP to the ER-Golgi boundary and the TGN. *J. Cell Sci* 108:2839–56.

Harris, A. S., J. P. Anderson, P. D. Yurchenco, L. A. D. Green, K. J. Ainger and J. S. Morrow. 1986. Mechanisms of cytoskeletal regulation: Functional and antigenic diversity in human erythrocyte and brain beta spectrin. *J. Cellular Biochem.* 30:51–70.

Harris, A. S., D. E. Croall and J. S. Morrow. 1989. Calmodulin regulates fodrin susceptibility to cleavage by calcium-dependent protease I. *J. Biol. Chem* 264:17401–17408.

Innis, M. A. and D. H. Gelfand (1990). *PCR Protocols.* San Diego, Calif., Academic Press.

Kelly, R. B. 1991. Secretory granule and synaptic vesicle formation. *Curr Opin Cell Biol* 3:654–60.

Kennedy, S. P., S. A. Weed, B. G. Forget and J. S. Morrow. 1994. A Partial Structural Repeat Forms the Heterodimer Self-Association Site of all b-Spectrins. *J. Biol. Chem* 269:11400–11408.

Koob, R., M. Zimmermann, W. Schoner and D. Drenckhahn. 1988. Colocalization and coprecipitation of ankyrin and Na+,K+-ATPase in kidney epithelial cells. *Eur J Cell Biol* 45:230–7.

Kordeli, E. and V. Bennett. 1991. Distinct ankyrin isoforms at neuron cell bodies and nodes of Ranvier resolved using erythrocyte ankyrin-deficient mice. *J Cell Biol* 114:1243–59.

Kordeli, E., J. Davis, B. Trapp and V. Bennett. 1990. An isoform of ankyrin is localized at nodes of Ranvier in myelinated axons of central and peripheral nerves. *J Cell Biol* 110:1341–52.

Kordeli, E., S. Lambert and V. Bennett. 1995. AnkyrinG. A new ankyrin gene with neural-specific isoforms localized at the axonal initial segment and node of Ranvier. *J Biol Chem* 270:2352–9.

Kreis, T. E. and R. Pepperkok. 1994. Coat proteins in intracellular membrane transport. *Curr Opin Cell Biol* 6:533–7.

Kunimoto, M., E. Otto and V. Bennett. 1991. A new 440-kD isoform is the major ankyrin in neonatal rat brain. *J Cell Biol* 115:1319–31.

Laemmli, U. K. 1970. Cleavage of structural proteins during the assembly of the head of bacteriophage T4. *Nature* 227:680–685.

Lambert, S., H. Yu, J. T. Prchal, J. Lawler, P. Ruff, D. Speicher, M. C. Cheung, Y. W. Kan and J. Palek. 1990. cDNA sequence for human erythrocyte ankyrin. *Proc. Natl. Acad. Sci (USA)* 87:1730–1734.

Luna, E. J. and A. L. Hitt. 1992. Cytoskeleton—plasma membrane interactions. *Science.* 258:955–964.

Lux, S. E., K. M. John and V. Bennett. 1990a. Analysis of cDNA for human erythrocyte ankyrin indicates a repeated structure with homology to tissue-differentiation and cell-cycle control proteins. *Nature* 344:36–42.

Lux, S. E., W. T. Tse, J. C. Menninger, K. M. John, P. Harris, O. Shalev, R. R. Chilcote, S. L. Marchesi, P. C. Watkins, V. Bennett, S. McIntosh, F. S. Collins, U. Francke, D. C. Ward and B. G. Forget. 1990b. Hereditary spherocytosis associated with deletion of human erythrocyte ankyrin gene on chromosome 8. *Nature* 345:736–739.

Matter, K. and I. Mellman. 1994. Mechanisms of cell polarity: sorting and transport in epithelial cells. *Curr Opin Cell Biol* 6:545–54.

Mays, R. W., K. A. Siemers, B. A. Fritz, A. W. Lowe, G. van Meer and W. J. Nelson. 1995. Hierarchy of mechanisms involved in generating Na/K-ATPase polarity in MDCK epithelial cells. *J Cell Biol* 130:1105–15.

McLean, I. W. and P. K. Nakane. 1974. Periodate-lysine paraformaldehyde fixative. A new fixative for immuno-electron microscopy. *Journal of Histochemistry and Cytochemistry* 22:1077–1083.

Michaely, P. and V. Bennett. 1993. The membrane-binding domain of ankyrin contains four independently folded subdomains, each comprised of six ankyrin repeats. *J Biol Chem* 268:22703–9.

Molitoris, B. A, R. Dahl and A. Geerdes. 1992. Cytoskeleton disruption and apical redistribution of proximal tubule Na(+)-K(+)-ATPase during ischemia. *Am J Physiol* 263:F488–95.

Morrow, J. S., C. Cianci, T. Ardito, A. Mann and M. T. Kashgarian. 1989. Ankyrin links fodrin to alpha Na/K ATPase in Madin-Darby canine kidney cells and in renal tubule cells. *J Cell Biol.* 108:455–465.

Morrow, J. S., C. D. Cianci, S. P. Kennedy and S. L. Warren (1991). Polarized Assembly of Spectrin and Ankyrin in Epithelial Cells. *Ordering the membrane Cytoskeleton Trilayer.* M. S. Mooseker and J. S. Morrow, Ed. New York, Academic Press. 227–244.

Morrow, J. S. and V. T. Marchesi. 1981. Self-assembly of spectrin oligomers in vitro: A basis for a dynamic cytoskeleton. *J Cell Biol.* 88:463–468.

Morrow, J. S., D. L. Rimm, S. P. Kennedy, C. D. Cianci, J. H. Sinard and S. A. Weed (1996). Of Membrane Stability and Mosaics: The Spectrin Cytoskeleton. *Handbook of*

Physiology. J. Hoffman and J. Jamieson, Ed., London, Oxford Press, (in press).

Nelson, W. J. and P. J. Veshnock. 1986. Dynamics of membrane-skeleton (fodrin) organization during development of polarity in Madin-Darby canine kidney epithelial cells. *J Cell Biol* 103:1751–1765.

Otto, E., M. Kunimoto, T. McLaughlin and V. Bennett. 1991. Isolation and characterization of cDNAs encoding human brain ankyrins reveal a family of alternatively spliced genes. *J. Cell Biol.* 114:241–253.

Pepperkok, R., J. Scheel, H. Horstmann, H. P. Hauri, G. Griffiths and T. E. Kreis. 1993. Beta-COP is essential for biosynthetic membrane transport from the endoplasmic reticulum to the Golgi complex in vivo. *Cell* 74:71–82.

Peters, L. L., K. M. John, F. M. Lu, E. M. Eicher, A. Higgins, M. Yialamas, L. C. Turtzo, A. J. Otsuka and S. E. Lux. 1995. Ank3 (epithelial ankyrin), a widely distributed new member of the ankyrin gene family and the major ankyrin in kidney, is expressed in alternatively spliced forms, including forms that lack the repeat domain. *J Cell Biol* 130:313–30.

Peters, L. L., F. M. Lu, K. M. John, A. Higgins, M. Yialamas, L. C. Turtzo, A. J. Otsuka and S. E. Lux. 1993. Cloning of a new epithelial-axonal ankyrin gene, ANK-3, in the mouse. *Mol. Cell Biol.* 4 supp:56a.

Peterson, G. L., Ed. (1983). *Protein determination.* Methods in Enzymology, Enzyme Structure, Part I. New York, Academic Press.

Platt, O. S., S. E. Lux and J. F. Falcone. 1993. A highly conserved region of human erythrocyte ankyrin contains the capacity to bind spectrin. *J Biol Chem* 268:24421–6.

Robinson, M. S. 1994. The role of clathrin, adaptors and dynamin in endocytosis. *Curr Opin Cell Biol* 6:538–44.

Sambrook, J., E. F. Fritsch and T. Maniatis (1989). *Molecular Cloning: A laboratory manual.* New York, Cold Spring Harbor Laboratory Press.

Smith, D. B. and K. S. Johnson. 1988. Single-step purification of polypeptides expressed in Escherichia coli as fusions with glutathione S-transferase. *Gene* 67:31–40.

Towbin, M., T. Staehelin and J. Gordon. 1979. Electrophoretic transfer of proteins from polyacrylamide gels to nitrocellulose sheets: procedures and some applications. *Proc. Natl. Acad. Sci* (*USA*) 76:4350–4354.

Van Why, S. K., F. Hildebrandt, T. Ardito, A. Mann, N. Siegel and M. Kashgarian. 1992. Induction and intracellular localization of HSP-72 after renal ischemia. *Am. J. Physiol.* 263:F769–775.

Weaver, D. C. and V. T. Marchesi. 1984. The structural basis of ankyrin function. I. Identification of two structural domains. *J Biol Chem* 259:6165–9.

Weaver, D. C., G. R. Pasternack and V. T. Marchesi. 1984. The structural basis of ankyrin function II. Identification of two functional domains. *J. Biol. Chem* 259:6170–6175.

Whitney, J. A, M. Gomez, D. Sheff, T. E. Kreis and I. Mellman. 1995. Cytoplasmic coat proteins involved in endosome function. *Cell* 83:703–713.

---

What is claimed:

1. An isolated nucleic acid molecule comprising contiguous codons encoding $Ank_{G119}$, wherein said encoded $Ank_{G119}$ has a molecular weight of about 116 kDa and comprises a region consisting of 13 repeats of a 33 residue structure, and further comprises a spectrin binding domain and a 5 kDa regulatory domain.

2. The nucleic acid molecule of claim 1, wherein the nucleic acid molecule encodes a human $Ank_{G119}$.

3. The nucleic acid molecule of claim 1, wherein the nucleic acid molecule encodes $Ank_{G119}$ comprising the amino acid sequence of SEQ ID NO: 2.

4. The nucleic acid molecule of claim 3, wherein the nucleic acid molecule comprises the sequence of SEQ ID NO: 1.

5. The nucleic acid molecule of claim 3, wherein the nucleic acid molecule consists of the sequence of SEQ ID NO: 1.

6. The nucleic acid of claim 3, wherein the nucleic acid molecule consists of nucleotides 131 to 3397 of SEQ ID NO: 1.

7. A vector comprising the nucleic acid molecule of any one of claims 1–6.

8. An expression vector comprising the nucleic acid molecule of any one of claims 1–6.

9. A host cell transformed or transfected with the vector of claim 7.

10. A host cell transformed or transfected with the expression vector of claim 8.

11. A method for producing an $Ank_{G119}$ protein comprising the step of culturing a host cell of claim 10 under conditions that allow expression of the protein.

* * * * *